United States Patent [19]

Eikefjord et al.

[11] Patent Number: 5,097,830
[45] Date of Patent: Mar. 24, 1992

[54] DEFIBRILLATOR WITH RELIABILITY VERIFICATION

[75] Inventors: Arild J. Eikefjord, Tananger; Helge Fossan, Stavanger, both of Norway

[73] Assignee: Laerdal Manufacturing Corporation, Portland, Oreg.

[21] Appl. No.: 502,481

[22] Filed: Mar. 30, 1990

[51] Int. Cl.[5] .............................................. A61N 1/39
[52] U.S. Cl. ................... 128/419 D; 128/734
[58] Field of Search ........................... 128/419 D, 734

[56] References Cited

U.S. PATENT DOCUMENTS

| Re. 30,387 | 8/1980 | Denniston et al. | 128/419 D |
|---|---|---|---|
| 4,094,310 | 6/1978 | McEachern et al. | 128/419 D |
| 4,202,340 | 5/1980 | Langer et al. | 128/419 D |
| 4,407,288 | 10/1983 | Langer et al. | 128/419 D |
| 4,432,375 | 2/1984 | Angel et al. | 128/419 D |
| 4,504,773 | 3/1985 | Suzuki et al. | 128/419 D |
| 4,823,796 | 4/1989 | Benson | 128/419 D |

OTHER PUBLICATIONS

Article entitled: "Standard for Automatic External Defibrillators," dated Nov. 14, 1989 from the Association for the Advancement of Medical Instrumentation.
Article entitled: "Microcomputers in Safety Technique, and Aid to Orientation for Developer and Manufacturer," published by Verlag Tüv Rheinland Gmblt, Köln in 1984.

Primary Examiner—Lee S. Cohen
Assistant Examiner—Kennedy J. Schaetzle
Attorney, Agent, or Firm—Klarquist, Sparkman, Campbell, Leigh & Whinston

[57] ABSTRACT

A defibrillator is described with dual processors for verifying the performance of the defibrillator and halting the application of a defibrillation pulse to a patient if a failure of system components is detected. In accordance with one aspect of the invention, verification is performed to determine whether a transfer relay switch should be closed to permit the application of a defibrillation pulse through the transfer relay switch to a patient. In addition, in one form of the invention, an electronic switch is provided in a series discharge circuit through the patient. Verification by both processors of proper conditions for application of a defibrillation pulse is required before a determination pulse is applied through the switch. In addition, an impedance circuit is provided with a mechanism for checking the accuracy of the circuit during operation of the defibrillator.

28 Claims, 10 Drawing Sheets

DEFIBRILLATOR WITH RELIABILITY VERIFICATION

BACKGROUND OF THE INVENTION

The present invention relates to defibrillators and, in particular, to portable defibrillators used under emergency circumstances to apply external defibrillation or therapeutic pulses to heart attack victims or patients suffering from ventricular fibrillation. More specifically, the present invention relates to defibrillators designed to detect potentially dangerous conditions within the defibrillator, such failures of certain components within the defibrillator that may cause a safety hazard to the operator or patient, and which disable the application of defibrillation pulses to a patient in the event such conditions exist.

Portable defibrillators have been in existence for a substantial period of time. One example of such a prior art defibrillator is disclosed in U.S. Pat. No. 4,823,796 to Benson, incorporated in its entirety by reference herein. Although damped sinusoidal and other defibrillation wave forms may be used in defibrillators, including the defibrillator of the present invention, the Benson patent discloses a defibrillator in which a trapezoidal shaped defibrillation pulse is applied to a patient. In accordance with the Benson patent, an electronic pulse delivery switch is in a series path which includes the patient and charge storage capacitors charged by a capacitor charging circuit. A single pole, double throw switch relay is also included in the Benson series circuit together with the electronic switch. Upon closing of the relay switches in response to a transfer relay signal, and following the rendering of the electronic switch conducting by a switch control signal, a discharge path is provided through the patient for discharging the charge storage capacitors. In the Benson patent, the electronic switch is rendered nonconducting to terminate the defibrillation pulse after the desired energy has been delivered to the patient. In this case, the resulting pulse is generally trapezoidal in shape. An energy selection circuit is provided for use in selecting the amount of energy to be applied to the patient by the defibrillation pulse. In addition, the Benson device has a voltage detection circuit provided for measuring the charge on the charge storage capacitors for use in determining when the capacitors are charged to the desired level for delivery of a defibrillation pulse of the selected energy.

The Benson defibrillator circuit has been incorporated into a commercially available defibrillator sold under the trademark Heartstart 1000 by Laerdal Medical Corp. of Armonk, N.Y., U.S.A. This particular defibrillator has a single microprocessor for controlling the performance of the defibrillator. In a conventional manner, the Heartstart 1000 defibrillator, and another commercially available defibrillator sold by Laerdal Medical Corp., the Heartstart 2000, monitors ECG signals from a patient and analyzes these signals according to a protocol. The purpose of this analysis is to determine when a patient is in cardiac distress of the type for which the application of a defibrillation pulse is appropriate, such as ventricular fibrillation and ventricular tachycardia. In addition to the protocol used in the Heartstart 1000 defibrillator, a number of protocols for analyzing ECG signals for shockable conditions are known, such as disclosed in U.S. Pat. No. 4,432,375 to Angel, et al. and in a report entitled "Standard for Automatic External Defibrillators," dated Nov. 14, 1989, from the Association for the Advancement of Medical Instrumentation of Arlington, Va.

The Heartstart 1000 and 2000 defibrillators are each operable in several modes, including a semi-automatic mode. In a semi-automatic mode, upon the determination of a shockable cardiac distress condition in a patient, a shock indicating message is visually displayed, and a shock indicating auditory message is provided to the operator of the defibrillator. In response to these signals, the operator may manually actuate a shock to initiate the delivery of a defibrillation pulse to a patient. The Heartstart 2000 defibrillator is also operable in a manual mode with the operator of the device simply monitoring the patient's condition without using the analysis protocol. A shock may then be initiated upon the determination that a shockable condition exists. In addition, automatic defibrillators are also known, including the Heartstart 1000 defibrillator, wherein ECG signals are automatically analyzed and a shock is applied without the intervention of the operator of the defibrillator, in the event a shockable cardiac distress is determined as a result of the analysis.

The Heartstart 2000 defibrillator, as well as other known defibrillators, typically monitor the impedance across the patient. If the impedance is outside of a desired range, an indication is provided that, for example, the patient coupling electrodes are incorrectly positioned or coupled to a patient.

The Heartstart 2000 defibrillator, as well as other defibrillators, have been used on many occasions to deliver defibrillation pulses to patients and bring the patients out of life threatening cardiac distress. However, for additional safety and enhanced performance, improvements in these devices are desirable. For example, in these devices there is a possibility of a failure of internal components which may result in the potential for delivering a defibrillation pulse to a patient in circumstances where the defibrillation pulse may not be appropriate.

The publication entitled "Microcomputers in Safety Technique, an Aid to Orientation for Developer and Manufacturer," published by Verlag Tüv Rheinland Gmblt, Köln in 1984, is a document relating to the use of microcomputers in safety-related applications, including medical electrical equipment, which would include defibrillators. The basic philosophy of this report is that no single fault which is assumed to arise will lead to a dangerous failure in the apparatus. Although providing general guidelines relating to safety design approaches, this particular article does not disclose specific designs for defibrillators. However, some of the general criteria set forth in this article are described below. In connection with software and restarts, for instance as a result of a "reset" situation, the article mentions the requirement of passing through a safe state. In addition, monitoring of the supply voltage of a system is mentioned in the article along with the taking of proper actions (e.g. going into a safe condition, switching off a processor, or switching to another channel) in the event the voltage falls below the specified limits of components in the system. In connection with two-channel structures, the article mentions the approach of comparing the results of complementary tests. In single channel structures, the article refers to the use of high level tests for monitoring ROM, RAM, input/output lines, CPU and also time-based and logic-based program monitoring. The article also makes reference to the use of diversified software. In addition, two-channel structures are described by the article as two independent functional units for carrying out a specified function. The article mentions that the functional units can be identical or that they can be built up in different ways using the principle of diversification (hardware diversification, software diversification, and time diversification). The article mentions that signals which are used or produced by both systems are continuously compared with one another for the purpose of fault detection. In an internal mutual comparison technique, for use in two-channel structures where both channels are implemented as computers, the article mentions that both computers are coupled together by either serial or parallel interfaces and exchange their input data, sometimes intermediate results, and their output data, for purposes of comparison. The comparison is carried out, according to the article, by and within both computers and if any nonequivalences are established by one or both computers, then a transition of the process to a safe state must take place. The computers are described by the article as comparing the signals computed by its partner and also the output signals with the signals computed by itself. In a hardware diversification technique, the results produced by two individual channels are compared with one another, and in the event of any discrepancy, a reaction is initiated for the purpose of a transition to a safe state. Although the Tüv article provides guidance for the development of products in safety-related applications, the article is not understood to suggest specific implementations of these guidelines in defibrillators.

Therefore, a need exists for an improved defibrillator and in particular, for such a defibrillator with reliability and performance verification features.

SUMMARY OF THE INVENTION

In accordance with one aspect of the present invention, a defibrillator for applying a defibrillation pulse to a patient suffering from cardiac distress includes a high voltage source and a defibrillator pulse discharge circuit for coupling the high voltage source in a series circuit with the patient to selectively deliver a defibrillation pulse from the high voltage source to the patient. The discharge circuit includes at least one relay means responsive to a transfer relay signal for shifting from a first position in which the relay means opens the series circuit to a second position in which the relay means closes to permit the passage of the defibrillation pulse to the patient. The defibrillator also includes a treatment indicating means for providing a treatment indicating signal corresponding to the patient being in a condition of cardiac distress of the type appropriate for the application of a defibrillation pulse to the patient. Also, a control circuit means is coupled to the treatment indicating means and to the relay means for providing the transfer relay signal in response to the treatment indicating signal. In one form, the control circuit means includes a first processor for providing a first relay control signal output in response to the treatment indicating signal, a second processor for providing a second relay control signal in response to the treatment indicating signal, the control circuit means also including a transfer relay circuit for providing the transfer relay signal to the relay means upon the occurrence of both of the first and second relay control signals. Consequently, in the event of an improper relay control signal from only one processor, the transfer relay signal is not provided to the relay means and the application of a defibrillation pulse under such conditions is prevented.

As another aspect of the present invention, the relay means may comprise a relay with first and second relay switches each shifting from the first to second positions in response to a common transfer relay signal. However, and most preferably, the relay means comprises first and second relays. In this case, the first switch relay may be responsive to a first transfer relay signal provided in response to the first relay control signal. In addition, the second relay switch may be responsive to a second transfer relay signal which is provided in response to the second relay control signal. In this latter case, the failure of a single transfer relay does not result in the inappropriate delivery of a defibrillation pulse to a patient.

As still another aspect of the present invention, the second processor may have an input for receiving the first transfer relay signal and may comprise means for preventing the delivery of the second transfer relay signal until the detection of the first transfer relay signal. In accordance with this aspect of the present invention, the sequential occurrence of the first transfer relay signal followed by the second transfer relay signal is required before the transfer relays are operated. As a result, further security is provided against the inadvertent application of a defibrillation pulse to a patient.

As a still further aspect of the present invention, the first processor may have an input for receiving the second transfer relay signal and the first processor may comprise means for terminating the first transfer relay signal in the absence of the occurrence of the second transfer relay signal within a predetermined time of the occurrence of the first transfer relay signal. Therefore, unless the second transfer relay signal occurs within a time window associated with the first transfer relay signal, the application of a defibrillation pulse to a patient is inhibited. This operational construction provides additional security against the inappropriate delivery of a defibrillation pulse to a patient.

As a further aspect of the present invention, the first processor may have an input for receiving the first transfer relay signal to confirm its occurrence and the second processor may have an input for receiving the second transfer relay signal to confirm its occurrence. Thus, in accordance with this aspect of the invention, the processors monitor the proper performance of the defibrillation circuit in that they verify the occurrence of the transfer relay signals in response to the relay control signal outputs from such processors.

As still another aspect of the present invention, although hardwired processors may be used, in the preferred form of the invention the processors comprise microprocessors. The use of dual microprocessors enhances the safety and portability of the defibrillator.

As another aspect of the present invention, the treatment indicating means may comprise a manually activated treatment initiator, such as a shock switch, for producing a treatment indicating signal upon activation thereof. The defibrillator may include an ECG monitoring mechanism, such as in the Heartstart 2000 defibrillator, for receiving and displaying ECG signals from the patient. In a semi-automatic mode, the ECG signals are analyzed as in the Heartstart 2000 and 1000 defibrillators and a shockable cardiac distress is indicated to the operator of the defibrillator. In response to this treatment indicating signal, the shock switch may be activated by the operator of the defibrillator. In a manual mode, as in the Heartstart 2000 defibrillator, the operator may monitor the patient directly, such as by monitoring the patient's ECG signals, so that when the operator recognizes the occurrence of cardiac distress, the operator may initiate a defibrillation pulse by activating the shock switch. In a fully automatic mode, the processors may analyze the ECG signals directly to produce the treatment indicating signals, which may comprise the first and second relay control signals, upon the determination of the existence of cardiac distress appropriate for treatment with a defibrillation pulse.

As a further aspect of the present invention, the defibrillator pulse discharge circuit may include an electronic switch in the series circuit. The electronic switch may be responsive to a transfer switch signal for switching to an electrically conductive state so as to allow the application of a defibrillation pulse through the switch to the patient. The first and second processors provide respective first and second switch control signals to a transfer switch circuit in response to the treatment indicating signal. Upon the occurrence of both of the first and second switch control signals, the transfer switch circuit provides the transfer switch signal to the switch to cause it to electrically conduct. With this approach, both of the processors produce the appropriate control signal before the electronic switch is operated. As a result, an improper switch control signal from only one of the processors is insufficient to cause the transfer switch circuit to provide the transfer switch signal.

As another aspect of the present invention, the first processor may receive the second switch control signal from the second processor and the second processor may receive the first switch control signal from the first processor. In addition, the second processor may comprise means for preventing the occurrence of the second switch control signal until the occurrence of the first switch control signal. In addition, the first processor may comprise means for terminating the first switch control signal in the absence of the occurrence of the second switch control signal within a predetermined time following the occurrence of the first switch control signal. In addition, the first and second processors may have respective inputs coupled to the transfer switch circuit for receiving the transfer switch signal so as to confirm the occurrence of the transfer switch signal in response to the first and second switch control signals.

As a still further aspect of the present invention, a voltage monitoring circuit may be provided for monitoring the voltage at the electronic switch. The voltage monitoring circuit is coupled to at least one of the processors such that improper voltage levels or magnitudes at the electronic switch are detected and communicated to the coupled processor. The processor may then inhibit the occurrence of the switch control signal to thereby prevent the operation of the switch upon the detection of improper voltage levels.

As a more specific aspect of the present invention, the electronic switch may comprise a switch having first and second switch elements or components with a circuit node therebetween. The voltage at the switch may be monitored at the circuit node. By comparing the node voltage with the voltage at the charge storage capacitors, a determination can be made as to whether either of the switch elements have failed.

As a further aspect of the present invention, the defibrillator may include an impedance measurement circuit coupled to one of the processors, such as the first processor, for measuring the impedance in the series circuit across the patient. The impedance measurement circuit may include means responsive to an impedance control signal for placing or adding a known impedance load in the impedance measurement circuit. The first processor comprises means for providing the impedance control signal. The processor, or equivalently the impedance measurement circuit, compares the impedance determined without the known load with the impedance determined with the known load. Because the added load is known, the measured impedance across the patient can be used to compute the expected impedance with the known load and compared with the impedance measured across the patient with the known load. If the results between the computed and measured impedances are inconsistent, that is not equal to one another within a range, an error in the impedance measurement circuit and a potential failure thereof is indicated. The activation of the defibrillation pulse may then be inhibited, for example by preventing the transfer relay control signals, preventing the transfer switch control signals, or both, in the event a potential failure is detected in the impedance circuit.

As another feature of the present invention, an event marker mechanism may be provided for indicating the occurrence of a significant event to data storage, for example to memory or a tape, for subsequent use in analyzing the performance of the defibrillator. Unlike conventional event marker mechanisms which are only operational when a defibrillator has its "power on" switch in the on position with the defibrillator being active, in accordance with the present invention the event marker may be used while the machine is off. That is, upon the occurrence of an event, an event marker switch or other mechanism may be activated. The activation of the event marker switch is sensed by the defibrillator circuitry and causes the circuitry to become active for a short period of time. During this time, an event marker or event indicating signal may be stored in the data storage. Time and date information from a real time clock is also typically stored at this time along with the event marker. The defibrillator then is returned to the off state following the storage of this information.

The present invention is directed to the above and other aspects and features of the present invention both alone and in combination with one another.

It is one object of the present invention to provide an improved defibrillator for applying defibrillation pulses to a patient.

Still another object of the present invention is to provide a defibrillator which is extremely safe and in which potential faults in the defibrillator are detected so as to prevent the inappropriate application of defibrillation pulses to a patient.

These and other objects, features, and advantages of the present invention will become apparent with reference to the following description and drawings.

DETAILED DESCRIPTION OF PREFERRED EMBODIMENTS

Figure 1:
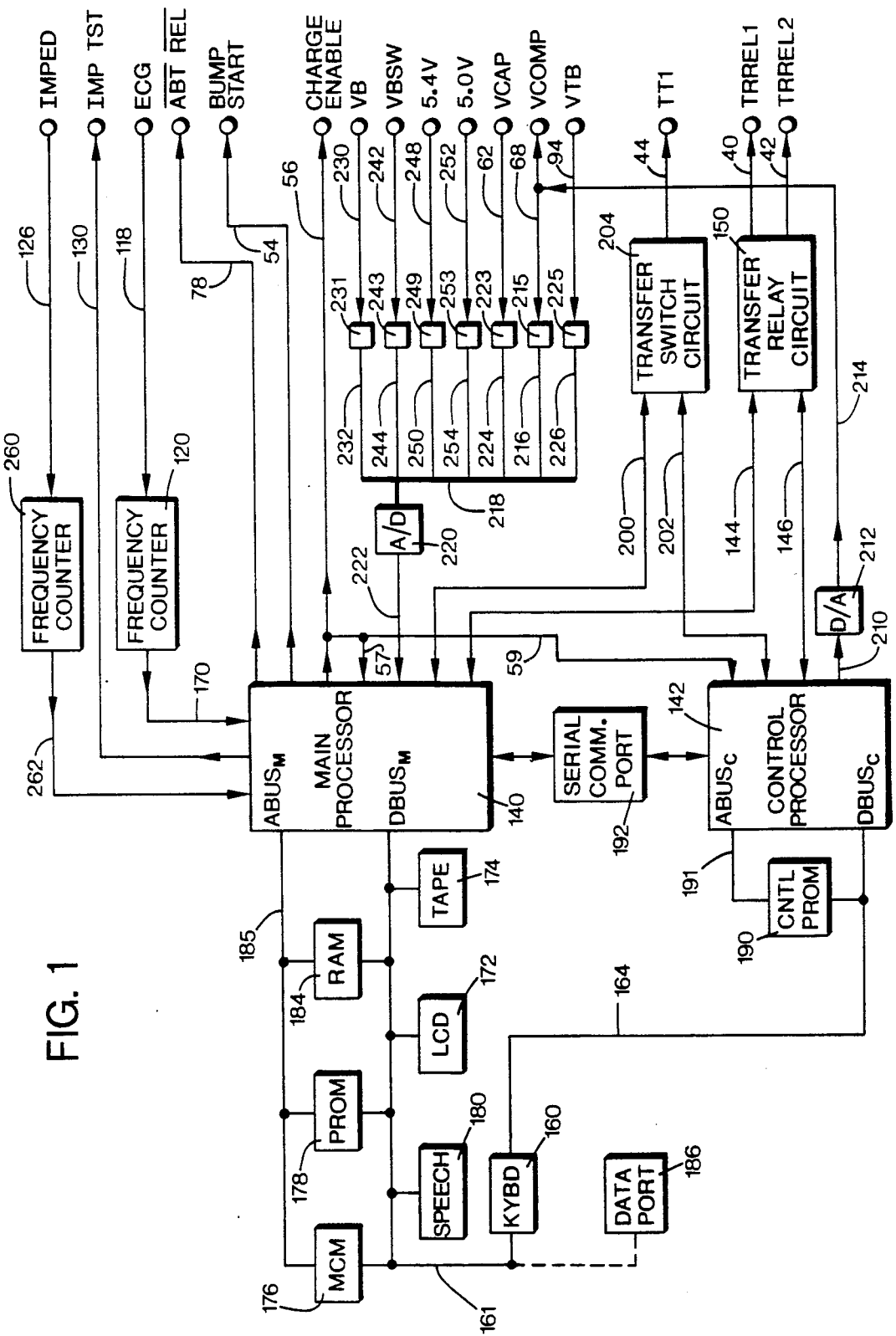
FIG. 1 is a block diagram of a control circuit of a defibrillator in accordance with the present invention utilizing dual microprocessors.
Figure 2:
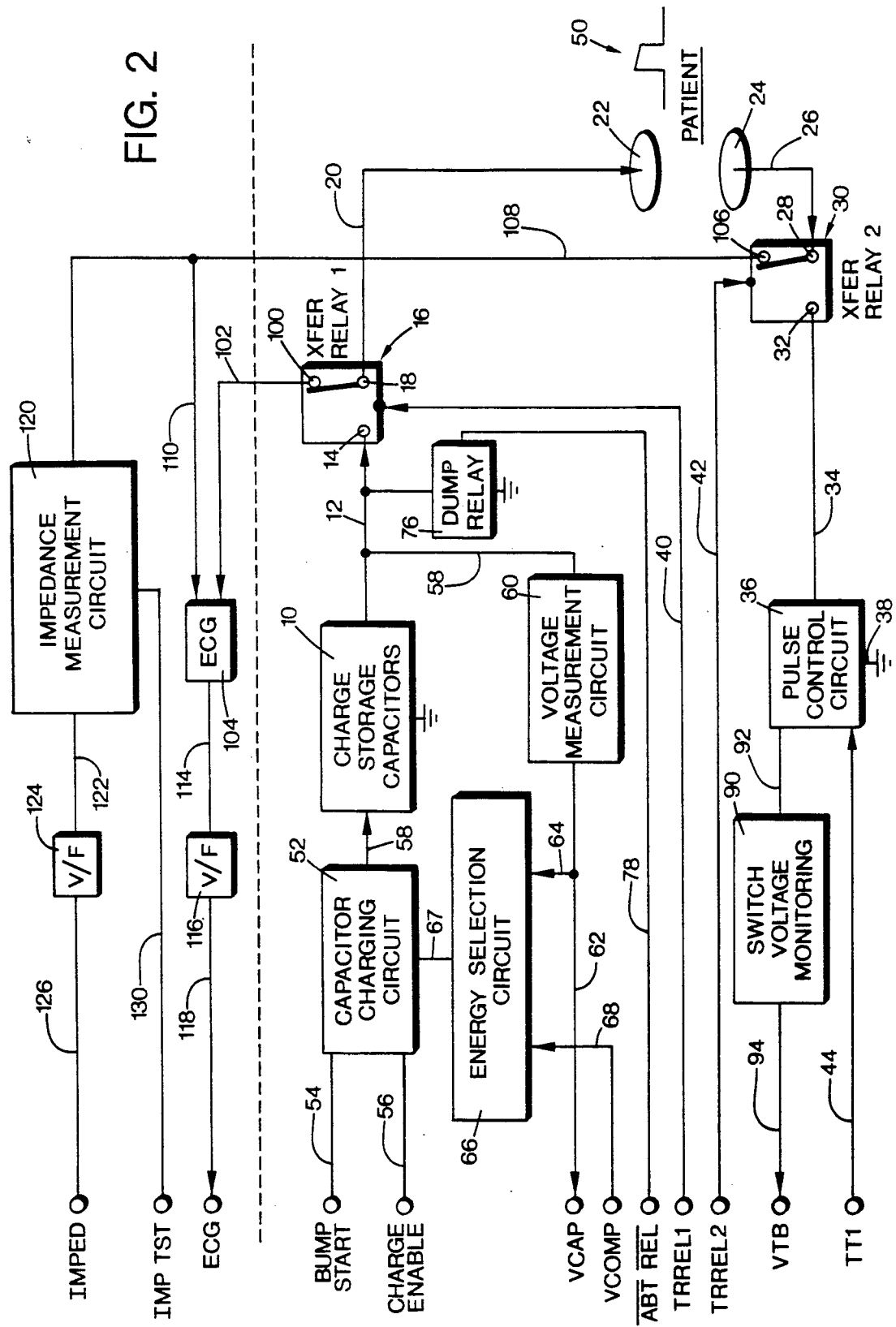
FIG. 2 is a block diagram of portions of a defibrillator circuit in accordance with the present invention for applying defibrillation pulses to a patient, detecting ECG signals from the patient, and determining the impedance across electrodes coupled to the patient.

With reference to FIGS. 1 and 2, one form of a defibrillator circuit includes a high voltage source such as charge storage capacitors 10 (FIG. 2), connected by a line 12 to an input terminal 14 of a pulse delivery switch or transfer relay 16. An output terminal 18 of the relay 16 is connected by a line 20 to a patient electrode 22 suitably positioned on the patient, such as at an apex location. Another electrode 24, such as at a sternum location on the patient, is connected by a line 26 to a terminal 28 of a second pulse delivery switch or transfer relay 30. A terminal 32 of the transfer relay 30 is connected by a line 34 to an optional pulse delivery switch mechanism or pulse control circuit 36, which in turn is coupled to ground potential at 38. The charge storage capacitors and transfer relays, together with the pulse control switch 36, if used, form a series circuit with the patient for use in selectively delivering a defibrillation pulse from the high voltage source to the patient.

In response to a first transfer relay signal (TRREL1) delivered on a line 40 to relay 16, relay 16 shifts to a defibrillation pulse delivery state in which the terminals 14 and 16 are coupled together and to the patient electrode 22. Similarly, when a second transfer relay signal (TRREL2) is delivered on a line 42 to the transfer relay 30, the relay 30 shifts to a pulse delivery state in which the terminals 28 and 32 are interconnected and coupled to the patient electrode 24. In addition, when a switch transfer signal (TT1) is delivered on a line 44 to the switch 36, the switch 36 is rendered conducting so as to complete the series path from the charge storage capacitors 10 and through the relay 16, the patient, the relay 30, the switch 36 and to ground potential. When this series circuit is closed, the charge storage capacitors 10 begin discharging through the patient. Assuming the switch 36 is included in the series circuit, the switch may be shifted to a nonconducting state, for example by removing the transfer switch signal on line 44. In this case, the series circuit is opened and the resulting defibrillation pulse is generally trapezoidal as indicated at 50 in FIG. 2.

The electrodes 22, 24 are conventional and are selectively coupled by the respective relays 16, 30 to the series circuit upon actuation of the relays. Although the relay mechanism illustrated in FIG. 2 comprises two separate relays, alternative configurations are also suitable, such as the double throw, double pole relay described below in connection with FIG. 3.

A capacitor charging circuit 52, in response to a bump start signal on line 54 and a charge enable signal on a line 56, which may either be manually or automatically generated, delivers a charging current on line 58 to the charge storage capacitors 10. Capacitor charging circuits are well known in the art. For example, a capacitor charging circuit of the type shown in FIG. 13 of U.S. Pat. No. Re 30,750 of Diack, et al. may be used. The capacitor charging circuit 52 may also be electrically isolated from the high voltage portions of the defibrillator circuit in a conventional manner. Although any suitable charging circuit may be used, the capacitor charging circuit shown in FIG. 2 is the same as the circuit used in the Heartstart 1000 defibrillator. This particular capacitor charging circuit requires the simultaneous occurrence of a bump start signal and a charge enable signal to commence operation. However, other forms of capacitor charging circuits simply utilize a charge enable signal for operation. The charge enable signal on line 56 is also fed back, by way of lines 57 and 59, to inputs of the respective main processor 140 and control processor 142. As a result, both of the processors are in a position to confirm that a proper charge enable signal has been provided on line 56.

The FIGS. 1 and 2 form of the invention also includes a voltage detection or measurement circuit 60, coupled by line 58 to the charge storage capacitors 10, for detecting or measuring the voltage on the charge storage capacitors. A signal corresponding to the measured voltage (VCAP) appears on a line 62 at an output of the voltage measurement circuit 60. The VCAP signal may also be coupled by a line 64 to an energy selection circuit 66, which in turn is coupled by a line 67 to the capacitor charging circuit. When the capacitors 10 are charged to a voltage which corresponds to a reference or threshold voltage setting (VCOMP) on a line 68, which is fed to the energy selection circuit 66, the energy selection circuit inhibits the capacitor charging circuit to stop the charging of the charge storage capacitors. The VCAP or signal appearing on line 62 may be used to provide a visual indication to an operator that the capacitors are fully charged for application of a defibrillation pulse to a patient. Alternatively, the VCAP signal may be automatically used, such as described in U.S. Pat. No. 4,432,375 of Angel, et al., in determining that the apparatus is ready to deliver an appropriate defibrillation shock to the patient.

The energy selection circuit 66 is optional and enables the control of the energy delivered to a patient as a result of a defibrillation pulse. By adjusting the signal VCOMP, the voltage at which full charge occurs and charging stops, the maximum voltage available for a defibrillation pulse is correspondingly adjusted and the energy available from the defibrillation can be controlled. That is, by controlling the duration of the transfer switch signal TT1 on line 44 and also by controlling the maximum voltage on charge storage capacitors 10, accurate control is achieved of the energy delivered to a patient by a defibrillation pulse. The VCOMP signal on line 68 is controlled by one of the FIG. 1 processors as described below. U.S. Pat. No. 4,823,796 to Benson describes several suitable energy control circuits.

In addition, as a safety feature, the defibrillator circuit of FIGS. 1 and 2 includes an abort or dump relay circuit 76 for selectively coupling the charge storage capacitors 10 to ground potential to discharge the charged storage capacitors at times when defibrillation pulses are no longer required. A signal ($\overline{ABT\ REL}$) on line 78 activates the dump relay 76 to selectively discharge the capacitors 10. The dump relay circuit 76 may be the same as the circuit described in U.S. Pat. No. 4,823,796 to Benson and may also be manually operable or automatically controlled.

A switch voltage monitoring circuit 90 is coupled by a line 92 to the switch circuit 36 for monitoring the voltage at the switch. A switch voltage indicating output from the monitoring circuit 90 appears on line 94 and is designated VTB. Assume the voltage VTB is at other than the desired magnitude or level for the particular portion or portions of the switch being monitored. In response to such unusual VTB signals, at least one of the processors may be operated to inhibit the application of a defibrillation pulse to the patient under these conditions. For example, any one or a combination of the TRREL1, TRREL2, and TT1 signals may be inhibited.

The first transfer relay switch 16 has a terminal 100 connected by a line 102 to one input of a conventional ECG monitoring circuit 104, such as of the type as used in the Heartstart 1000 defibrillator. Similarly, the transfer relay 30 has a terminal 106 coupled by a line 108 and line 110 to another input of the ECG circuit. When the relays 16 and 18 are in a patient monitoring position as shown (and the transfer relay signals are absent from lines 40 and 42), the ECG circuit 104 is coupled by the electrodes 22, 24 to the patient for picking up ECG signals from the patient. Separate ECG electrodes, instead of the electrodes 22 and 24, may of course be used for detecting the ECG signals. By using the relays 16 and 30 to couple the ECG circuitry to the patient, the ECG circuitry is automatically disconnected from the patient when the transfer relays are shifted to a charge delivery state in series with the charge storage capacitors 10. The output signal from ECG circuit 104 typically comprises a voltage output corresponding to the ECG signals. The voltage signal may be converted by a voltage to frequency convertor 116 to, for example, a frequency modulated ECG output signal on line 118. The voltage to frequency convertor 116 may serve to isolate the components on the line 118 side of the voltage to frequency converter 116 from the high voltage components of the apparatus.

The line 108 from transfer relay 30 is also coupled to an input of an impedance measurement circuit 120. Circuit 120 is conventional insofar as it produces an output voltage on line 122 corresponding to the impedance between electrodes 22 and 24 across the patient. This signal is converted by voltage to frequency converter 124 to an impedance output signal (IMPED) on line 126, which corresponds to the impedance across the patient. However, unlike conventional impedance measurement circuits heretofore used in defibrillator applications known to the inventors, in response to an impedance test signal (IMP TST) on a line 130 to the impedance measurement circuit, a known impedance load is coupled to the impedance circuit, for example in parallel or in series with the patient. If the impedances measured with and without the known load may be determined and compared as explained below. The impedances with and without the load are not consistent, an error or fault may have occurred in the impedance measurement circuit. If a fault in the impedance measurement circuit is detected, then the defibrillator may be shut off or, alternatively, the application of defibrillation pulses to a patient may be inhibited. Again, blocking or inhibition of the defibrillation pulses can be accomplished by withholding any one or a combination of the TRREL1, TRREL2 and TT1 signals.

With reference to FIG. 1, the illustrated defibrillator includes first and second processors 140, 142 which are respectively denominated a main processor and a control processor. The functions of either processor may be performed by the other processor if desired. The processors 140, 142 preferably comprise commercially available microprocessors such as a microprocessor model 80C188 for main processor 140 and a microprocessor model 80C31 for control processor 142, both from Intel Corporation. The main and control processors 140, 142 thus form a part of a control circuit for controlling the operation of the defibrillator. Although hard wired circuitry may be used, in particular for the control processor, the use of microprocessors facilitates the production of a compact cost effective defibrillator, in particular, a portable defibrillator which is highly suitable for use in the field under emergency circumstances.

Upon the determination that the patient is in a condition of cardiac distress of the type appropriate for the application of a defibrillation pulse to the patient, the main processor 140 produces a first relay control signal on an output line 144. The control processor similarly, in response to a treatment indicating signal, provides a second relay control signal on an output line 146. A transfer relay circuit 150 receives the relay control signals on the respective lines 144, 146, and in response thereto, provides the TRREL1 and TRREL2 signals on their respective lines 40, 42. In general, unless both of the relay control signals are delivered to the transfer relay circuit 150, the signal or signals required to activate the transfer relay means (FIG. 2) are not provided by the transfer relay circuit. Consequently, an improper switch transfer relay signal on only one of the lines 144, 146 is insufficient to cause the relays 16, 30 to close and the safety of the defibrillator is enhanced.

Figure 3:
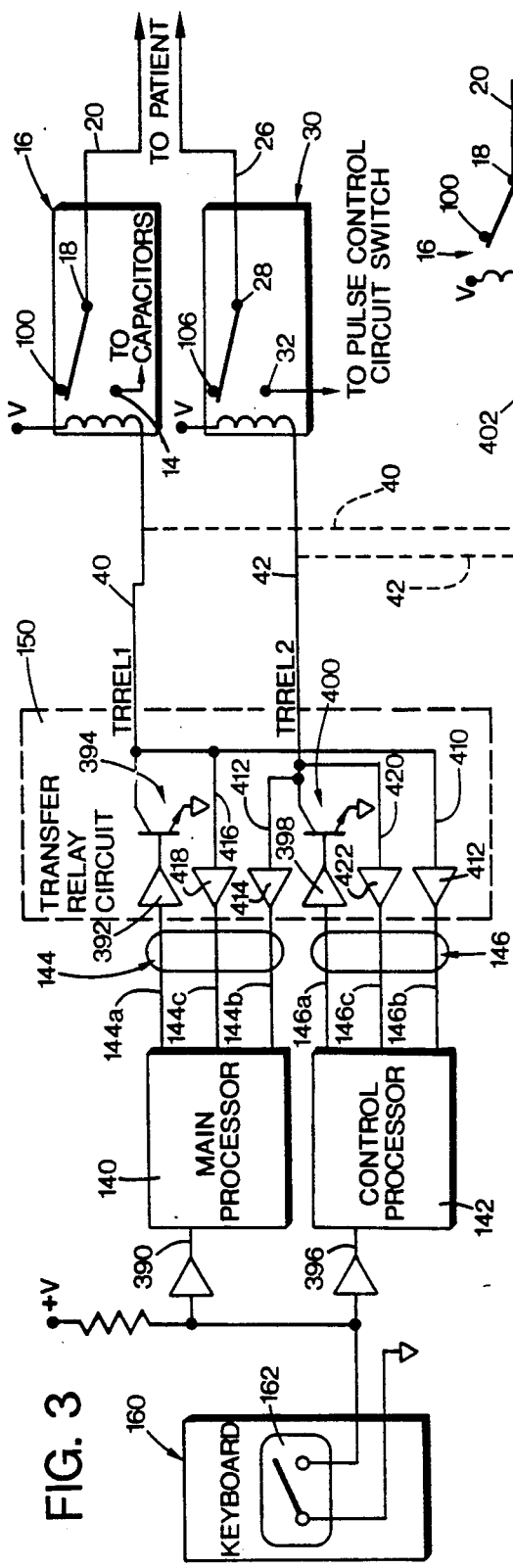
FIG. 3 is an electrical schematic diagram of one form of transfer relay circuit shown in block form in FIG. 1.
Figure 7:
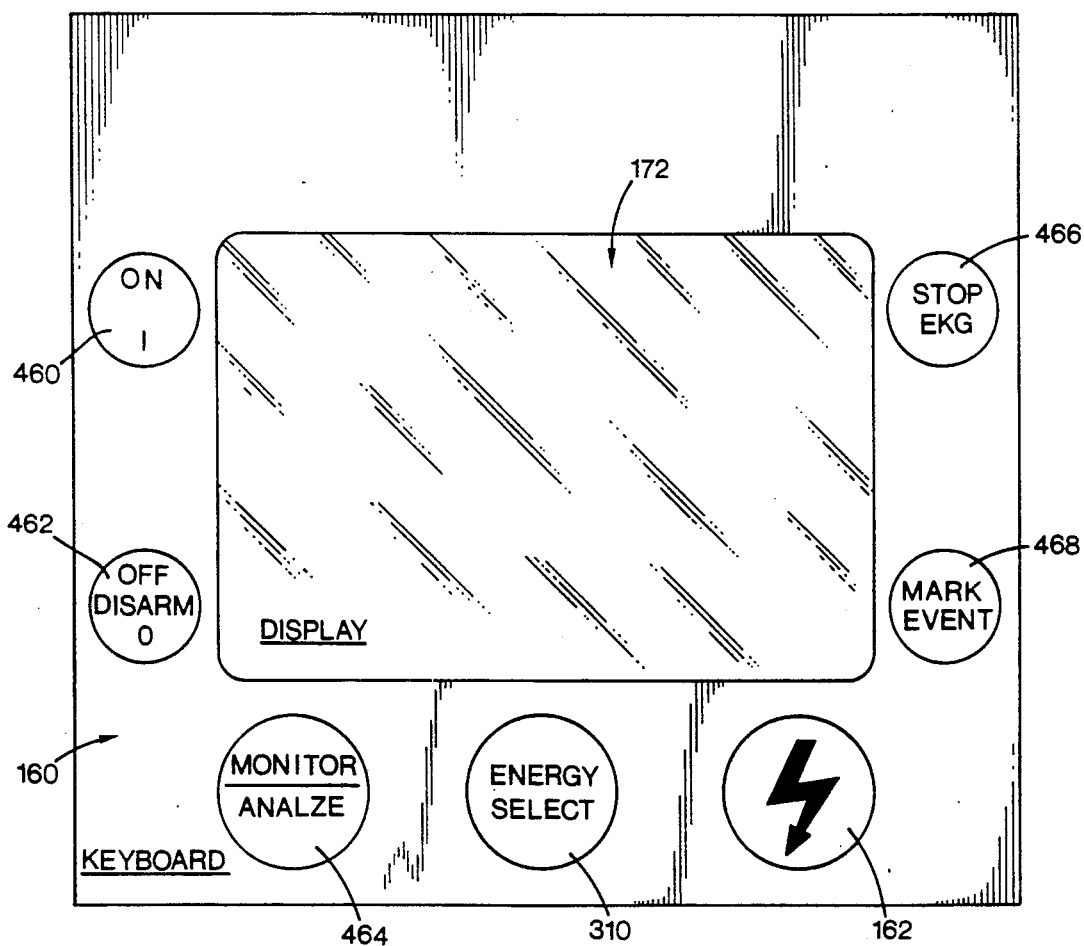
FIG. 7 is a plan view of one form of a display and keyboard used in the defibrillator of FIGS. 1 and 2.

As shown in FIG. 1, a data entry device such as a keyboard 160, is coupled by a data bus 161 to a data bus input/output of the main processor 140 and also by a data bus 164 to the data bus input/output of the control processor 142. As described in greater detail below, the keyboard may include a manually activated treatment initiator, such as a shock switch 162 (FIGS. 3 and 7). When the treatment initiator is activated, a treatment indicating signal is delivered to both the main and control processors 140, 142. The transfer relay control signals on lines 144 and 146 are provided by the processors in response to the treatment indicating signal if other conditions, explained below, for the application of a shock to the patient are met. The ECG signals on line 118 are decoded by frequency counter 120 to provide ECG signals on a line 170 which are suitable for input to the main processor. In a known manner, these ECG signals may be displayed on a liquid crystal display 172 coupled by a display driver (not shown) to the bus 161. All or selected portions of the ECG signals may be recorded on a data channel of a tape recording module 174 coupled to the bus 161 and also in a medical control module 176 which is also coupled to the bus 161. The medical control module is conventional and comprises mass storage memory for storing ECG and other information.

In a manual mode, the operator of the defibrillator may simply monitor the patient and the display 172 for ECG signals indicative of a shockable cardiac distress in the patient. When these conditions are observed, the shock switch on keyboard 160 is activated to produce the treatment indicating signal to initiate the defibrillation pulse application sequence. A PROM 178 is also provided for storing the main processor program including the protocol used in analyzing ECG signals in the event the main processor is capable of ECG signal analysis. ECG signal analysis implemented by hardware circuits, such as in the Heartstart 1000 defibrillator may alternatively be used. When in this mode, the ECG signals are automatically analyzed for cardiac distress, such as ventricular fibrillation and ventricular tachycardia, appropriate for treatment with a defibrillation shock. In a semi-automatic mode, upon the analysis of the ECG signals and a determination that a shockable condition exists, an operator message indicating this fact is displayed on the LCD 172 display. In addition, an auditory message may be provided to the operator by a speech synthesis circuit 180, coupled to bus 161, to also indicate this condition. The operator may then activate the shock switch 162 to initiate the defibrillation pulse sequence. In an automatic mode, the shock switch is eliminated and the processor 140 internally generates a shock initiating signal upon a determination from the analysis of the ECG signals that a shockable condition exists. A random access memory 184 shown in FIG. 1, coupled to bus 161, provides memory space for temporary storage of data by the main processor 140. The components 176, 178 and 184 are also coupled to an address bus 185 and to an address input/output of the processor 140. An optional data or communications port 186 is also provided and may be used, for example, with a modem for transmission of ECG and other information to a remote site. The commercially available Heartstart 2000 defibrillator also has a tape, display, speech synthesis circuit, keyboard, RAM, PROM and medical control module. A second PROM 190, designated as CNTL PROM in FIG. 1, is provided for storing the program for the control processor 142. PROM 190 is coupled to bus 164 and to an address bus 191 in communication with an address input/output of the control processor. In addition, a communications path, such as a serial communication port 192, is provided to permit communications between the two microprocessors so that cross checking of the operability and performance of the two microprocessors may take place.

If the defibrillator is of the type with a switch such as switch 36 (FIG. 2), in the defibrillator pulse discharge circuit through the patient, such a switch is responsive to a transfer switch signal (TTI) on line 44 as previously explained. In this case, the main processor 140 provides a first switch control signal on a line 200 in response to the treatment indicating signal. In addition, the control processor 142 provides a second switch control signal on a line 202 in response to the treatment indicating signal. A transfer switch circuit 204 receives the switch control signals on the lines 200, 202. In general, upon the occurrence of both of the switch control signals, the switch transfer signal is provided by the transfer switch circuit 204 on the line 44. However, if an improper switch control signal is provided on only one of the lines 200, 202, a switch transfer signal is not provided by the switch transfer circuit. Consequently, under such conditions, an improper switch control signal on only one of the lines 200, 202 does not cause the switch 36 to close and the application of the defibrillation pulse is inhibited.

In the illustrated control circuit, the control processor 142 has an output 210 for providing a signal corresponding to the VCOMP reference signal. The digital signal on line 210 is converted by a digital to analog converter 212 to analog form for transmission on a line 214 to the VCOMP line 68. The VCOMP signal on line 68 is fed by a line 216 through a signal conditioning circuit 215 (e.g. a filter and voltage divider) and by a line 216 to one of a group of lines 218 leading to an analog to digital converter 220. The resulting digital signal corresponding to the VCOMP signal is transmitted from analog to digital converter 220 on a bus line 222 to a data input of the main processor. This allows the main processor to confirm that a proper VCOMP signal has been transmitted by the control processor to the energy selection circuit 66 (FIG. 2). If a proper VCOMP signal has not been transmitted, the main processor senses this discrepancy and can inhibit the application of a defibrillation pulse by blocking the switch control transfer switch control signal on line 200 or the transfer relay control signal on line 144.

Similarly, the VCAP signal is transmitted from line 62 (FIG. 1) to a signal conditioning circuit 223 and over a line 224 to one of the lines 218. Similarly, the VTB signal is fed from line 94 through a signal conditioning circuit 225 to a line 226 and then to one of the lines 218. Lines 224 and 226 are coupled by lines 218, the analog to digital convertor 220 and bus line 222 to the main processor. By comparing the VCAP signal to the VTB signal, as explained below, the main processor is able to determine whether the switch 36 has failed. That is, if the voltage monitored at the switch and represented by the VTB signal is at a magnitude or level other than expected for a particular VCAP signal, an error in the voltage measuring circuit 60, the switch monitoring circuit 90, or the switch 36 is indicated. In this case, the main microprocessor may inhibit the defibrillator from applying a defibrillation pulse.

Figure 6:
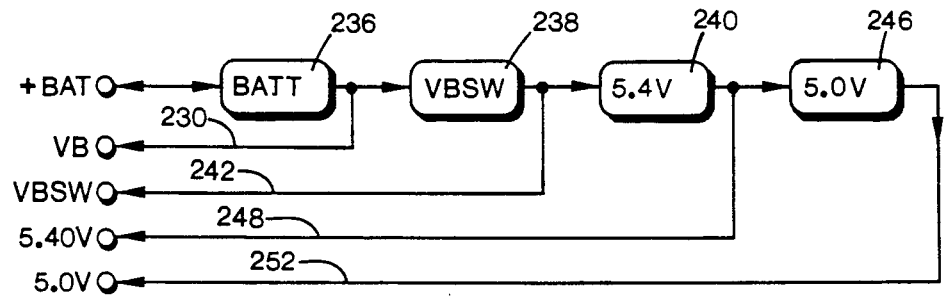
FIG. 6 is an electrical schematic diagram of one form of power supply circuit utilized in the defibrillator of FIGS. 1 and 2.

Power supply voltages from the power supply circuit, described below in connection with FIG. 6 are also monitored by the main processor. In particular, the battery voltage (VB) is fed via lines 230, a signal conditioning circuit 231, a line 232, one of the lines 218, analog to digital converter 220 and bus line 222 to an input of the main processor 140. If the battery voltage becomes too low for satisfactory operation of the apparatus, warning signals may be displayed at display 172. In addition, the defibrillator may be shut off if the voltage drops below an acceptable level. The line 230 is taken from the output of the system battery 236 as shown in FIG. 6. The battery is coupled through a power on relay switch 238 to a first voltage regulator 240 and to a line 242. The line 242 is coupled through conditioning circuit 243, to a line 244, one of the lines 218, the analog to digital converter 220 and bus line 222 to an input of the main processor. By monitoring the VBSW signal on line 242, the main processor can determine whether the relay 238 has failed. The regulator 240 (FIG. 6) produces an output at a first regulated voltage magnitude, in the case 5.4 V, which is fed to a second voltage regulator 246. The output of voltage regulator 240 is also fed to a line 248. The line 248 is coupled through a signal conditioning circuit 249 to a line 250 (FIG. 1), one of the lines 218, the analog to digital convertor 220 and bus line 222 to the main processor. Similarly, the output of voltage regulator 246 (FIG. 6), in this case at 5.0 V, is fed on a line 252 to a signal conditioning circuit 253 (FIG. 1), to a line 254, one of the lines 218, the analog to digital converter 220, and one bus line 222 to the main processor. The voltages from regulators 240 and 246 are thus monitored by the main microprocessor. The main microprocessor will inhibit the operation of the defibrillator if the output of the voltage regulators is outside of a predetermined range. For example, the main microprocessor may be operable to inhibit the defibrillation operation of the output of the 5.4 V regulator 240 is above 5.6 V or if the output of the 5.0 V regulator 246 is above 5.3 V. All of the circuitry in the defibrillator is designed to operate within the range of voltages permitted by the voltage regulators. With this design, if the regulator 246 fails, the voltage in the apparatus is set by the output of regulator 240 at a level which is insufficient to cause failure of the components of the defibrillator. Similarly, if the regulator 240 fails, the regulator 246 limits the voltage to 5.0 V. By using a dual voltage regulator approach, a failure of one of the regulators is not only monitored, such a failure does not cause the failure of other components in the system because the other regulator limits the voltage. If a low voltage from the regulators is detected by the main processor 140, the defibrillator may be reset with a low voltage message being displayed on the display 172.

The measured impedance signals on line 126 are fed to a frequency counter 260, which produces a digital signal on line 262 corresponding to the measured frequency. As explained below, the main processor transmits the impedance test signal (IMP TST) on line 130 to cause the inclusion of a known load in the impedance circuit. The microprocessor then compares the impedance without the load to the impedance with the load to determine whether they are consistent. If not, a failure is indicated in the impedance circuit and operation of the defibrillator may be inhibited until such time as consistent impedance measurement again occur or correction of the failure is made.

The impedance measurement circuit is used to detect whether the transfer relays 16, 30 are in the monitoring position and whether proper contact exists between the electrodes and the patient. In addition, the impedance measurement circuit is used in determining the length of the defibrillation pulse to be administered to the patient.

Figure 5:
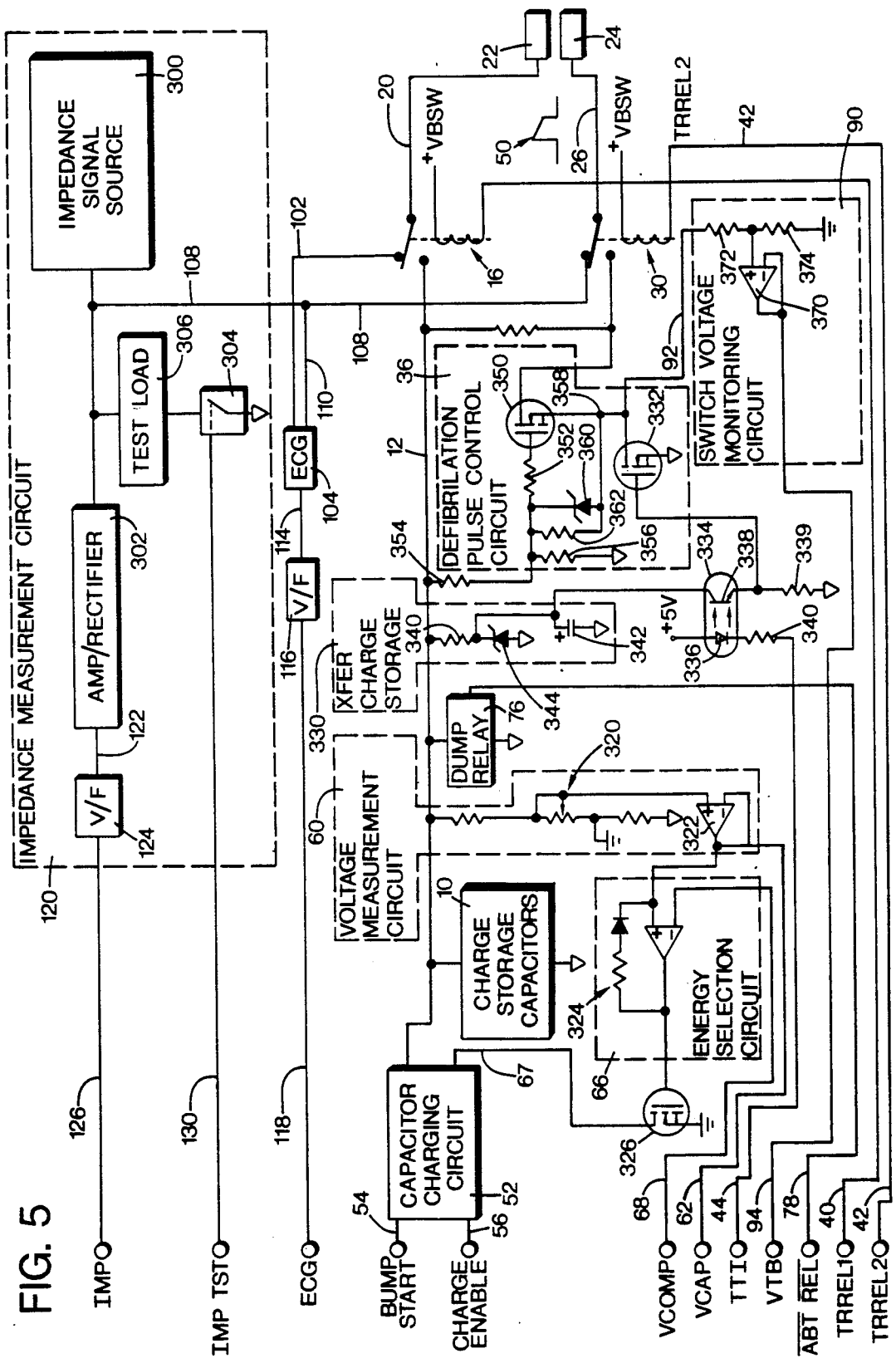
FIG. 5 is a more detailed electrical schematic diagram of the portions of the defibrillator circuit shown in FIG. 2.

With reference to FIG. 5, the illustrated impedance measurement circuit includes an impedance signal source 300, which typically applies a constant current at 70 kHz to line 108 and thus across the patient. The resulting signal is amplified and rectified by a amplifier/rectifier indicated at 302. The resulting signal on line 122 is converted to an impedance indicating frequency signal at the voltage to frequency converter 124. The main microprocessor 140 (FIG. 1) computes the impedance from the impedance signal provided at line 126.

A fault in the impedance measurement circuit is detected by switching in a known load, for example in parallel with the patient. A relay switch 304, responsive to the impedance test signal on line 130 from the microprocessor, is used to selectively couple the test load 306 in parallel with the patient. Typically, the test load comprises a 47 ohm resistor. From the measured impedance without the test load and given the fact that the test load is known, the expected measured impedance with the test load can be computed. The computed patient impedance with the test load is compared to the measured patient impedance with the test load. Equivalently, the impedances may be measured with the test load and the expected patient impedance without the load may be computed. The computed result may then be compared with the measured impedance without the test load for consistency. The measured impedance must be within a tolerance range, for example, plus or minus 10% of the calculated result, for the defibrillator to continue to operate. If not, a failure in the impedance measurement circuit or in components associated with this circuit is indicated.

Typically, impedance measurement circuit testing is performed when the defibrillator is turned on and at each time the measured impedance changes from an out of range impedance to an impedance within a defibrillation or monitoring range. Although these ranges may be varied, the defibrillation impedance range may be set at from about 25 to 200 ohms and the monitoring impedance range be set at from about 301 to 2,500 ohms. With this setting, impedances at 0 to 24 ohms, 201 to 300 ohms and in excess of 2,500 ohms are out of range and will result in the display of a check electrodes signal on the display 172 of FIG. 1. In addition, the main microprocessor typically tests the impedance every 100 milliseconds, or at some other interval, except when the relays 16, 30 are in the defibrillation pulse application state, at which time the impedance measurement circuit is disconnected from the patient. The control processor 142 receives impedance samples from the main processor by way of the communication port 192 (FIG. 1). The control processor verifies that the impedance is within the defibrillation range. In addition, before the control processor will allow charging of the capacitors 10 to start, it will verify that the test load 306 has been inserted and that the impedance was tested with a correct result.

For a given patient impedance, the operator of the defibrillator may select a desired energy to be applied to the patient utilizing an energy select switch 310 (FIG. 7) or other input device. Typically, the user is allowed to select energy levels from 5 to 360 J with 256 incremental selections being possible. Once the energy selection has been made, the microprocessor determines the reference voltage signal VCOMP and the duration of discharge of the capacitors (by controlling the TTI signal) to control the energy delivered to the patient to match the selected level. U.S. Pat. No. 4,823,796 to Benson describes, in connection with FIG. 3 thereof, a similar selection approach. The user interactive energy selection approach may be eliminated with the defibrillator determining the amount of energy being applied to the patient in accordance with a protocol. Alternatively, a single or limited range of energies may be applied, such as 50J, 200 J or 360 J, with a selection being allowed between these levels.

With further reference to FIG. 5, the illustrated voltage measurement circuit includes a voltage divider 320 coupled to the charge storage capacitors 10 for detecting the voltage on the capacitors. The capacitor voltage is amplified by an amplifier 322. The output of amplifier 322 comprises the VCAP signal on line 62 and is also fed to one input of the energy selection circuit 66. The illustrated energy selection circuit comprises a comparator circuit 324 for receiving both the VCAP and the VCOMP signals. When the VCOMP signal is exceeded by the VCAP signal, corresponding to the charging of the capacitors to the desired charge, a signal is delivered to the gate of a field-effect transistor 326. The transistor 326 then turns on, which results in a drop in the level of the voltage on line 67, and inhibits the capacitor charging circuit 52 so that charging the capacitors 10 is halted.

A transfer charge storage circuit 330 is included in the circuit of FIG. 5 for providing a transfer voltage signal to a field-effect transistor 332 of the defibrillation pulse control circuit 36. The circuit 330 may be coupled to the line 12 for charging by the capacitor charging circuit 52 as the charge storage capacitors 10 are charged. A transfer switch 334 selectively couples the transfer charge storage circuit 330 to the transistor 332. The transfer switch 334 may comprise a conventional optoisolator with a photo diode portion 336 and a photo responsive transistor portion 338. The anode of diode portion 336 is coupled to the 5 V supply while the cathode of this diode portion is connected through a resistor 340 to the line 44. At times when a defibrillation pulse is to be applied to a patient, the transfer switch signal TTI is applied to line 44 and causes the optoisolator 334 to conduct. The emitter of transistor portion 338 is coupled to ground through a resistor 339 and to the gate of the transistor 332. A transfer voltage signal from transfer charge storage circuit 330 is then applied to the gate of the field-effect transistor 332, causing this transistor to conduct with a result as explained below.

The transfer charge storage circuit 330 is like the corresponding circuit described in U.S. Pat. No. 4,823,796 to Benson and includes a circuit path from line 12 through a resistor 340 to the optoisolator switch 334. A charge storage capacitor 342 is coupled in parallel to the line between resistor 340 and the optoisolator for storaging charge as the charge storage capacitors 10 are charged by the capacitor charging circuit 52. A zener diode 344, with its cathode connected to the line between resistor 340 and the optoisolator 334 and its anode grounded, limits the maximum voltage on the capacitor 342 and also the voltage applied to optoisolator 62 so that its breakdown voltage is not exceeded while allowing the application of adequate voltage to the gate of the field-effect transistor 332 to turn it on.

The defibrillation pulse control circuit 36 includes a second field-effect transistor 350 in addition to field-effect transistor 332. Each of the transistors 332, 350 may be insulated gate bipolar transistors. The gate of transistor 350 is connected through a pair of resistors 352, 354 to line 12 and also through a resistor 356 to ground. The resistors 352, 354 and 356 effectively bias the circuit so that, when field-effect transistor 332 is off, approximately one-half of the value of the voltage on the charge storage capacitors 10 is across each of the transistors 332, 350. That is, the voltage at node 358 between the source of transistor 350 and the drain of transistor 332 is approximately one-half of the voltage on the charge storage capacitors. The gate to source voltage of transistor 350 is limited by a 14 volt zener diode 360 connected as shown. A resistor 362, coupled between the gate and source of the transistor 350, provides a path for current flow to the node 358 and to the drain of transistor 332. In response to the transfer switch signal TTI on line 44, the transistors 332 and 350 conduct and provide a path for a defibrillation pulse through the relay 16, the electrode 22, the patient, and electrode 24, the relay 30 and the switch comprised of switching elements 332 and 350.

The voltage at line 358 is monitored by a switch voltage monitoring circuit 90. The illustrated circuit 90 includes a buffer amplifier 370 having its noninverting input coupled through a resistor 372 to the line 92 and through another resistor 374 to ground. The output of amplifier 370 comprises the VTB signal on line 94 and corresponds to the voltage at the node 358.

During charging of the charge storage capacitors 10, voltage VCAP on the charge storage capacitors 10 and the transistor block voltage VTB are monitored every 40 milliseconds. With the illustrated buffer amplifier 370 and with resistors 372 and 374 at, respectively, 50 Meg ohms and 232K ohms, VTB is expected to be approximately equal to VCAP divided by 4. Of course, other relationships between these voltages may exist if other circuit configurations are used. In the event VTB is not within an expected range of VCAP/4 (e.g. plus or minus 50%) then an indication is provided that a failure exists in the defibrillation pulse control circuit. For example, one failure can be the failure of either transistor 332 or transistor 350. If a failure is detected, charging is stopped, the application of a defibrillation pulse is blocked, and a service mandatory message is displayed at the display 172 to indicate that there is a problem with the transistor voltage. In addition, after the delivery of a shock, VCAP is immediately read and compared to an expected value. If the remaining VCAP voltage on the charging capacitors 10 is not within a range (e.g. approximately plus or minus 20%) of the expected voltage following the delivery of a defibrillation pulse of the selected energy, an appropriate message is displayed and further defibrillation pulses may be blocked. In addition, if the fully charged VCAP voltage is less than the selected voltage VCOMP, or at least within a range of this voltage, for example plus or minus 10%, then a failure in the charging circuit or in the energy selection circuit is indicated. In this case, a suitable message is displayed and the application of a defibrillation pulse to a patient is blocked.

Although the illustrated defibrillation pulse control circuit is shown with an electronic switch comprised of a pair of switching elements, in this case transistor 332 and transistor 350, a single electronic switch or another form of switch (e.g. a mechanical switch) may be used. In this case, the voltage would not be monitored at a node between two switching elements, but at some other appropriate location, if voltage monitoring is desired. Also, it should be noted that the electronic switch may be eliminated, in which case the transfer relays 16 and 30 would be used to control the application of the defibrillation pulses to the patient. Again, however, the use of an electric switch facilitates the control of energy delivered to a patient and more specifically, facilitates the use of trapezoidal defibrillation pulses. In addition, the electronic switch provides a further backup in the event the relays 16 and 30 fail or in the event of a failure of a single pole, double throw relay if such a relay is used instead of the separate relays 16, 30.

With reference to FIG. 3, one form of a suitable transfer relay circuit 150 is shown in greater detail. In a simple form, a signal path is provided through the transfer relay circuit from a first output 144a of the main processor 140 to the first transfer relay signal output at line 40 from the transfer relay circuit. In connection with this signal path, and assuming other conditions for delivery of a defibrillation shock to a patient are correct (e.g. proper impedance measurements), in response to the activation of shock key 162 and the delivery of the resulting treatment indication signal to an input 390 of the processor 140, a first relay control signal is fed from the main processor to a first relay control signal output thereof on line 144a. This signal is buffered by a conventional digital logic gate 392 and fed to the base of a switching transistor 394. Transistor 394 becomes electrically conductive in response to the first relay control signal and results in an output of the first transfer relay signal (TRREL1) on line 40. Similarly, in response to the input of the treatment indicating signal at an input 396 to the control processor, a second relay control signal is fed from an output of the control processor along a line 146a, a signal path through the transfer relay circuit 150, and to the line 42. That is, the second relay control signal is buffered digital logic gate 398 and fed to the base of a switching transistor 400. In response to this signal, transistor 400 conducts and provides the second transfer relay signal (TRREL2) on line 42. In this simple form of relay transfer circuit, two signal paths are provided, each from a respective one of the microprocessors to a respective transfer relay in the defibrillator pulse delivery series circuit. As an option, and as shown in FIG. 3, the signals on lines 40 and 42 may be fed through an AND gate 402 and to a control input 404 of a double pole, double throw relay. In this case, the relay has respective relay switches 16 and 30 which each shift from first to second positions in response to a common transfer relay signal, namely the signal on line 404. This latter approach also utilizes the two transfer relay signals and thus requires consistent outputs from each of the microprocessors 140 and 142 in order for the relay to operate.

In addition, in the circuit of FIG. 3, the second processor has an input 146b for receiving the first transfer relay signal. That is, the first transfer relay signal is fed from line 40 on a line 410 and through a digital logic gate 412 to an input 146b of the second processor. The second processor may comprise means for preventing the delivery of the second relay control signal on line 146a, and thus for preventing the second transfer relay signal on line 42, until the detection of the first transfer relay signal. This reliability or safety of the defibrillator as an additional verification is required before the second transfer relay signal occurs. Similarly, the first processor 140 includes an input 144b for receiving the second transfer relay signal from line 42. This second transfer relay signal is fed on a line 412 through a digital logic gate 414 and to the input 144b. The first processor may comprise means for terminating the first transfer relay signal in the absence of the occurrence of the second transfer relay signal within a predetermined time of the occurrence of the first transfer relay signal. This prevents the first transfer relay signal from remaining active for a long period of time during which the erroneous occurrence of a second transfer relay signal could cause the inappropriate closing of the transfer relays 16, 30.

In addition, the line 40 is coupled by a line 416 through a digital logic gate 418 to another input 144c of the main processor 140. This allows the main processor to monitor the occurrence of the first transfer relay signal in response to the first relay control signal on line 144a. In the absence of the first transfer relay signal under these circumstances, a failure of transistor 394 or the digital logic gate 392 is indicated. In the same manner, the line 42 is coupled by a line 420 through a digital logic gate 422 to an input 146c of the second processor. This allows the control processor to monitor the occurrence of the second transfer relay signal in response to the second relay control signal on line 146a. The absence of the second transfer relay signal in response to the second relay control signal indicates a failure of the transistor 400 or of the digital logic gate 398. Again, reliable verification of the safe operation of the defibrillator is provided through the use of a transfer relay circuit configured as shown in FIG. 3.

It should be noted that a proper treatment indicating signal utilizing the circuit of FIG. 3 requires the activation of the shock switch 162 after the defibrillator has been charged and is ready to deliver a shock. In addition, the shock switch 162 in this example must be held down or activated for a predetermined time, such a 0.15 seconds, to prevent triggering of a shock in the event the shock switch is accidentally bumped. In addition, the activation of the shock switch for the required hold time is detected by both microprocessors before the treatment cycle commences.

Figure 4:
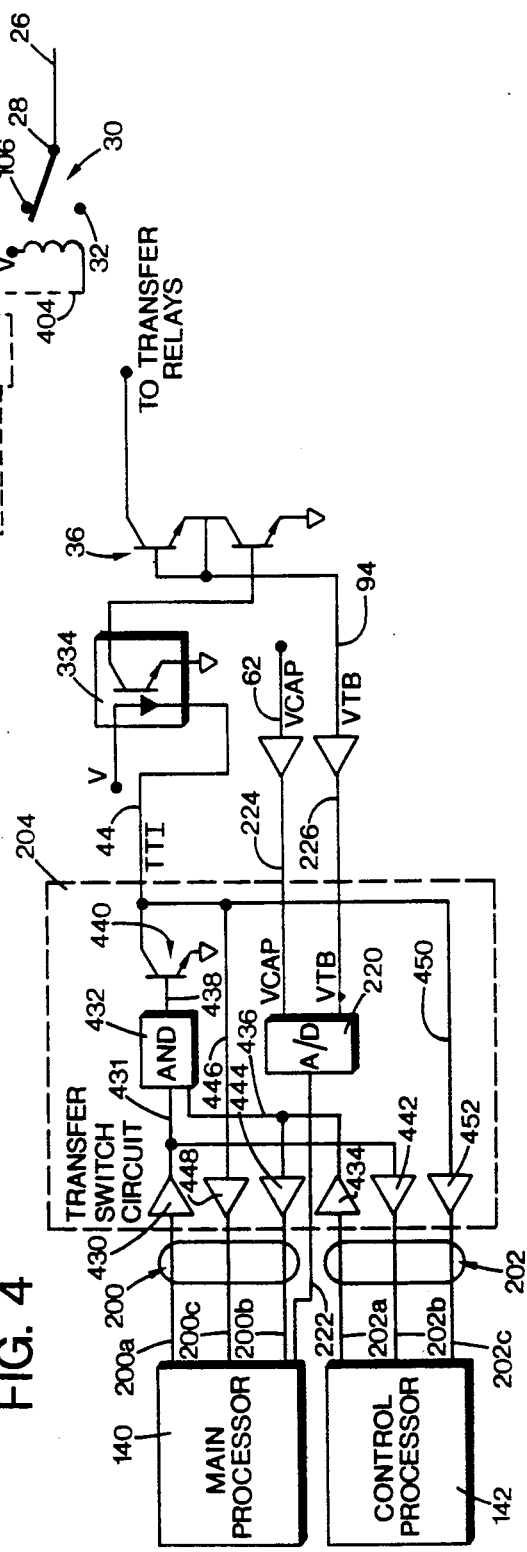
FIG. 4 is an electrical schematic diagram of one form of transfer switch circuit shown in block form in FIG. 1.

With reference to FIG. 4, a suitable transfer switch circuit 204 is illustrated. In general, the main processor has a first output 200a at which a first switch control signal is delivered in response to the treatment indicating signal, assuming other conditions for delivery a shock (e.g. proper impedance) are met. The first switch control signal passes through a digital logic gate 430 and is delivered to one input 431 of an AND gate 432. Similarly, the control processor 142 has a first output 202a from which a second switch control signal is delivered in response to the treatment indicating signal, again assuming the other conditions for the application of a defibrillation pulse are met. The second switch control signal is fed through a digital logic gate 434 and to another input 436 of the AND gate 432. When both of the switch control signals are present, in this case at a high logic level, at AND gate 432, the positive or high logic output from AND gate 432 is fed on a line 438 to a transistor 440 and causes this transistor to conduct. As a result, the transfer switch signal (TTI) is provided on line 44.

The first switch control signal is also fed from line 431 through a digital logic gate 442 and to an input 202b of the control processor. The control processor 142 may comprise means for preventing the occurrence of the second switch control signal on line 202a until the occurrence of the first switch control signal detected at input 202b. This provides added safety against the inadvertent activation of the AND gate 432 as a result of an improper switch control signal. Similarly, the second switch control signal is coupled from the line 436 through a digital logic gate 444 to an input 200b of the main processor 140. The main processor may comprise means for terminating the first switch control signal in the absence of the occurrence of the second switch control signal, as detected at input 200b within a predetermined time following the occurrence of the first switch control signal. This again provides added safety to the defibrillator as the first switch control signal does not remain for an indefinite time during which time an improper second switch control signal may occur.

In addition, the line 44 is coupled by a line 446 and a digital logic gate 448 to an input 200c of the main processor 140. The line 44 is also coupled by a line 450 through a digital logic gate 452 to an input 202c of the control processor. This enables the processors 140, 142 to monitor the occurrence of the TTI signal on line 44 and to confirm that this signal has occurred at the proper time. An incorrect TTI signal provides an indication that a failure has occurred in the AND gate 432 or the transistor 440.

In connection with the above transfer switch circuit 204, assume one or both of the transistors 332, 350 are always conducting due to a fault in the transistors or in the transistor driving circuitry. During charging and before activation of the transfer relays, the VTB is compared to the VCAP voltage. If one of the transistors is conducting under these circumstances, VTB will be much less or much greater than VCAP/4 and charging will be aborted. Assume the transistor 332 breaks down during charging and starts conducting. In this case, transistor 350 will start conducting and the measured VTB will be at ground potential and a fault is detected. If transistor 350 breaks down, transistor 332 may also break down depending upon the VCAP voltage. In this case, VTB will either equal VCAP or ground and a fault is detected. In both cases, the transfer relays will be open and there will be no hazard to the patient. Also assume the transistors 332, 350 do not conduct due to a fault in the transistors or in the driving circuitry. In this case, the series circuit through the patient will remain open by the transistors 332, 350 and no shock will be given to the patient. This fault will be detected by the processor reading the VCAP voltage immediately after the shock. Because the VCAP voltage will not have dropped, the fault will be detected. Finally, assume that the transistors do not turn off again following the shock delivery time due to errors in the transistor or driving circuitry, including the processors. In this case, all of the energy stored by the capacitors 10 will be delivered to the patient. This is typically approximately 25% more energy than should be delivered, depending upon the circumstances, and would not result in an injury to the patient. This error is detectable by reading the VCAP voltage signal after the shock and the system can then be shut down.

FIG. 7 illustrates one form of display 172 and keyboard 160 utilized in the defibrillator of FIGS. 1 and 2. The keyboard 160 typically comprises a membrane switch having a number of switch positions. A power on switch 460 is provided for turning on the power to a power relay (not shown) and thus to the defibrillator. An off/disarm switch 462 is also provided. When this switch is depressed, the processors 140, 142 cause the power relay to open to turn off power to the defibrillator and the abort relay 76 is operated to discharge the capacitors 10. A state selection switch 464 is also provided. When in a monitoring mode, ECG signals are displayed on display 172 for review. Typically a dot matrix integral backlight display is used. This display may be a conventional split screen display with the lower half of the screen containing commands and messages and the upper half of the screen displaying ECG signals. In an analyze mode, the main processor 140 analyzes the ECG signals to determine if shock treatable cardiac distress exists. If the ECG analysis indicates a treatable cardiac rhythm is present, charging of the capacitors commences if other conditions (e.g. proper impedance) are met. In a manual mode, depression of this key commences charging of the capacitors without the ECG analysis.

The energy select key 310 is used to select the energy which will be applied to a patient. When the machine is in a semi-automatic mode, one form of energy select mechanism allows the application of 200J or 360J to the patient by a defibrillation pulse. If the defibrillator is in a manual mode, energy levels at 50J, 200J or 360J are typically selectable. Again, as previously explained, a wide range of energy levels may also be selected. Keyboard 160 also includes the shock initiation switch 162 as previously explained. The stop EKG switch 466 operates in a conventional manner to freeze portions of the ECG signals. When the defibrillator is in the manual mode, actuation of the stop EKG switch results in the continuous display of the active most recent 4.5 seconds of ECG information in the upper half of the screen. In addition, the most recent 4.5 seconds of ECG information occurring prior to the activation of the stop EKG switch is displayed on the lower half of the screen for further study by the operator of the defibrillator. If the defibrillator is in the semi-automatic mode, the stop EKG switch causes the most recent 3.0 seconds of ECG information to be frozen on the left side of the screen with 1.5 seconds of active ECG information being continuously displayed on the right side of the screen. The Heartstart 2000 defibrillator also operates in this manner to permit the freezing of portions of the ECG information on a display screen.

The mark event switch 468 signals the main processor 140 to note time and data information from a real time clock. In addition, the processor 140 causes the storage of an event marker in the data being stored by the defibrillator upon activation of switch 468. For example, a high frequency beep, may be stored on the tape being recorded by the tape recorder 174 (FIG. 1) to cause the printing of an asterisk or other indicator on a hard copy of the information when dumped from the tape. Similarly, a marker may be stored in the memory of MCM module 176 (FIG. 1). If the defibrillator is on when the event marker switch is actuated, 6 seconds of ECG signals centered around the time of activation of the event marker is written into the MCM module. The use of event markers during the operation of a defibrillator are known in the art, for example, in the Heartstart 2000 defibrillator. However, as described in connection with FIGS. 8 and 9, a unique aspect of the present invention is its capacity to mark events while the machine is off, that is prior to the activation of the power to the defibrillator using on switch 460. One may, for example, mark the time one arrives at the location of a victim prior to activating the defibrillator power switch 460.

Figure 8:
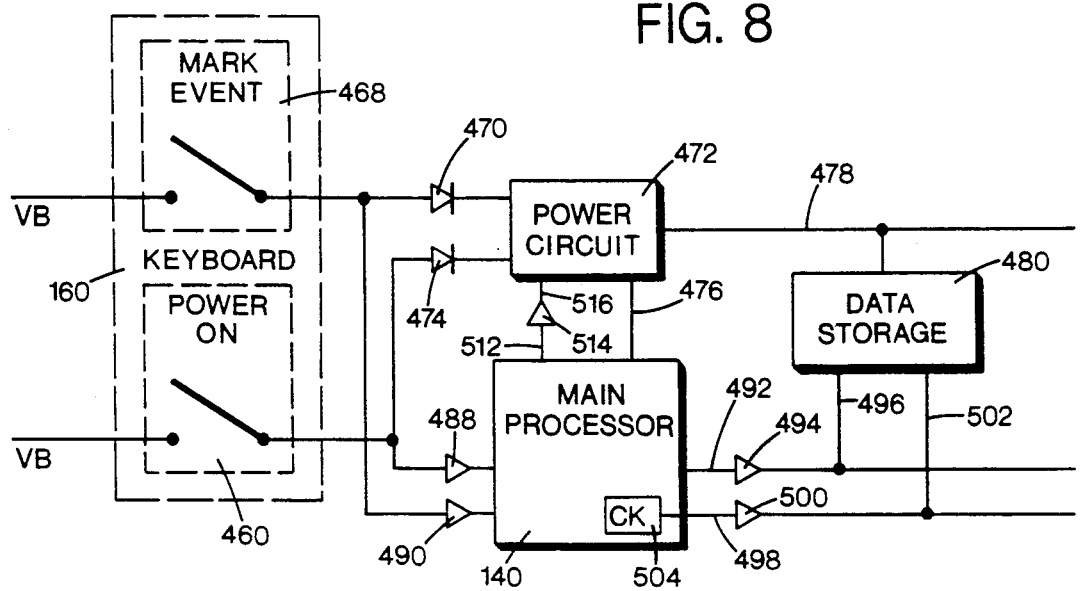
FIG. 8 is an electrical schematic diagram illustrating the operation of the mark event feature of the defibrillator of the present invention.
Figure 9:
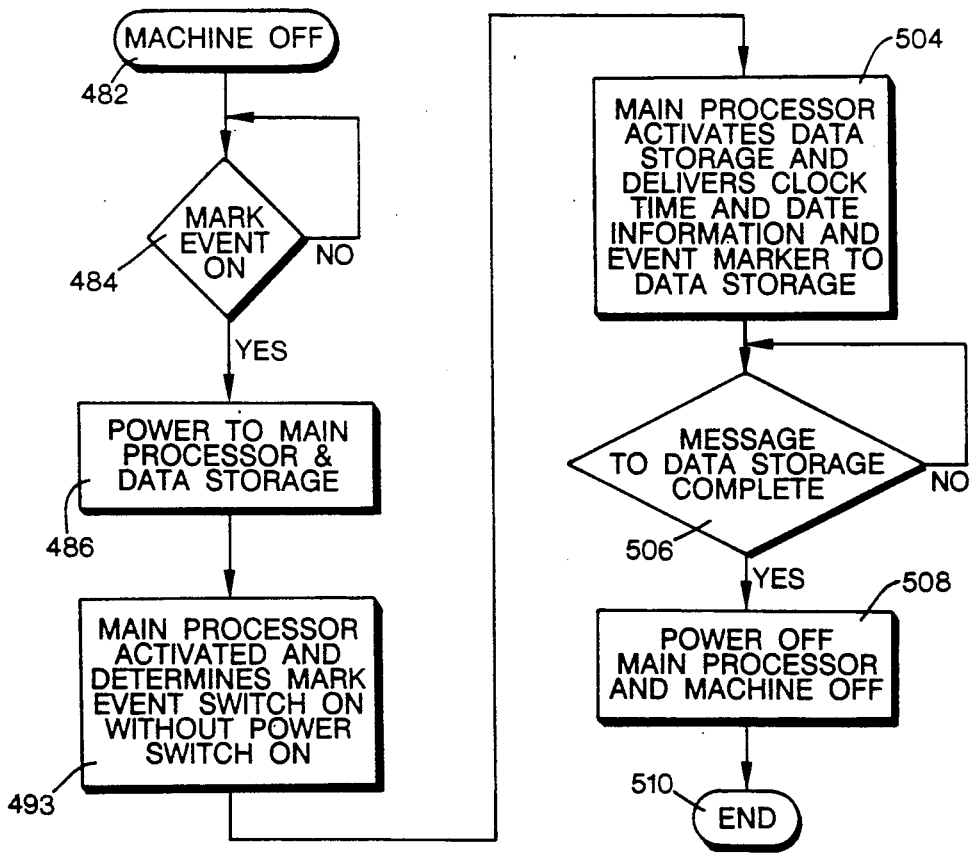
FIG. 9 is a flow chart describing the operation of the mark event feature of the present invention.

With reference to FIGS. 8 and 9, assume the mark event switch 468 is closed while the power switch 460 is off. In this case, the battery voltage VB is coupled through mark event or activator 468 and a diode 470 to the power circuit 472 of the apparatus. The power circuit 472 is activated by either the power on switch, through a diode 474 to the power circuit 472 or by the mark event switch 468. When the power circuit is activated, the main processor 140 (as well as the control processor 142) are supplied with power as indicated schematically by way of power connection line 476. In addition, power is delivered to the other components of the apparatus as indicated by the line 478 coupled to the data storage components 480 of the apparatus, such as the tape recorder 174 and the memory control module 176 (FIG. 1). This sequence of events is indicated by flow chart blocks 482, 484 and 486 in FIG. 9. Following activation, because the main processor has inputs coupled by way of digital logic gates 488, 490 to the respective power on and mark event switches 460, 468, the main processor determines that the mark event switch 468 has been activated without activation of the power on switch 460. This step is indicated by block 493 in FIG. 9. In response to this determination, the main processor 140, by way of an output path including line 492, digital logic gate 494 and a line 496, activates the tape recorder, memory control module or other data storage mechanism 480. In addition, by way of a path including a line 498, a digital logic gate 500 and a line 502, time and date information from a real time clock 504 is delivered to the data storage mechanism for storage therein. In addition, main processor 140 also delivers an event marker to the data storage 480 (along bus 161, FIG. 1) for storage along with the time and date information. As a result, although the nature of the event is not recorded, the fact that an event of significance occurred at a particular time and date is entered into the data storage. This occurs even though the power on switch is off and the defibrillator is not active to deliver a defibrillation pulse to a patient or receive ECG information. This last sequence of events is indicated by block 504 in FIG. 9. After the message has been stored in data storage 480, as indicated by block 506 in FIG. 9, the power circuit is shut off by the main processor, the defibrillator is off (see block 508), and the sequence ends (block 510). To turn off the power circuit, a signal is delivered from main processor 140 on a line 512 through a digital logic gate 514 and a line 516 to the power circuit.

Under these conditions, the mark event switch in effect acts as a power on switch to temporarily activate the defibrillator to allow the storage of the event marker and time and date information. Instead of recording both time and date information, either of these types of information, or other information, may be recorded along with the event marker.

With reference to FIGS. 10-13, the programming of the main processor 140 and control processor 142 will next be described.

Following power up to the main processor 140 and at the start of the program, an initialize block 520 is reached. At block 520, the hardware components of the system are set to their initial states, the internal clock in the main processor is set, and a number of system self tests are performed. For example, memory is tested, registers are tested by marching test patterns through the registers with the results being checked, instructions that set flags are performed with the results being checked, arithmetic and logical operations are performed and checked to test the arithmetic logic unit of the microprocessor, and the addressing of the system is checked. In addition, internal timers of the microprocessor are tested by counting variables between counter state changes with the count values being compared to an expected result. Also, a verification is made that the processor 140 is receiving signals of the ECG and impedance monitoring lines 118, 126. Moreover, the supply voltages from the power supply circuit (FIG. 6) are checked. In addition, the measured capacitor voltage VCAP at start up is checked to verify that it is less than an initial value, such as 100 V. Furthermore, the input/output lines of the microprocessor are read and compared to a safe state. For example, a confirmation is made that the charge enable signal is at a state which does not activate the capacitor charging circuit 52 (FIG. 2), the $\overline{\text{ABT REL}}$ line 78 is monitored to confirm that it is not coupled to ground insuring the dump relay is in a safe state, and the inputs and outputs on lines 144 and 200 are monitored to confirm that the transfer relay control signals, transfer switch control signals, the transfer relay signals and the transfer switch signal are correct. In addition, the real time clock (e.g. 504 in FIG. 8) is checked to determine whether it is running. In addition, the keyboard is checked to determine whether all of the keys except the "power on" key 460 or the "mark event" key 468 are active. If any of these tests reveal an incorrect condition, an appropriate message is displayed on display 172 and the defibrillator is inhibited from applying a defibrillation pulse to a patient.

On an ongoing basis, for example every 5 milliseconds, during timer interrupts, the state of the processor input/output lines are monitored with the appropriate message being displayed in the event a failure or incorrect state is detected. In addition, the impedance is tested periodically by way of impedance input 262 to determine that it is at the correct level. During these timer interrupts and as the system is operated, the ECG signals are read and displayed, the impedance signals are read and impedance is calculated, the keyboard is read, messages are sent to the control processor by way of serial communication port 192 (FIG. 1), the status of the processor input/output lines are monitored, and the supply voltage circuit (FIG. 6 is monitored). In the event of any significant errors, the defibrillator is blocked from applying a defibrillation pulse to the patient and an indication of the failure is provided to the user by way of the display. Finally, at block 520, the processor 140 state is set to the monitoring mode and a path 522 is followed to the monitoring block 524 in FIG. 10.

In the monitoring mode, ECG signals are delivered to the main processor and displayed for review by the operator of the defibrillator. In addition, continued checking of the impedance, state of the hardware components, and input/output lines to the processor 140 continues. In errors are detected during the monitoring state, or for that matter during any other state the system is in, an appropriate message is displayed and the defibrillator is shut down in the event of critical errors. Also, at any time, a path 526 may be followed to an off state 528 in the event power is shut down by operating the off/disarm switch 462 in FIG. 7. From the monitoring mode 524, the processor 140 flow chart follows a path 530 to an analyzing mode 532. The analyze mode is reached by depressing the analyze switch 464 on the keyboard 160 (FIG. 7). In this state, which is optional in that the operator of the defibrillator may simply monitor the ECG signals directly, the defibrillator analyzes the ECG signals for rhythms suitable for the application of a defibrillation pulse. The defibrillator typically provides a visual and auditory indication upon the detection of a shockable rhythm. The operator of the defibrillator may then manually initiate charging the capacitors by depressing a charging switch (not shown in FIG. 7). In this case, the charging block 536 would be reached. However, in a semi-automatic mode, a flow path 533 is followed from block 530 to an analyzing/charging block 535. If the system includes this block, (which is typically included in an automatic system), upon the detection of a treatable rhythm, charging of the charge storage capacitors 10 automatically starts in that a flow path 537 is followed to a charging block 536. When charging of the capacitors is complete, a path 538 is followed to a ready block 540 corresponding to the processor 140 state wherein the capacitors 10 are ready to deliver a defibrillation pulse to a patient. From the ready state 540, a flow path 542 is followed to a discharge block 544. The discharge block corresponds to the defibrillator being in a state for discharging the defibrillation pulse to a patient. At any time during the blocks 535, 536, 540, in the event that a determination is made that conditions are not suitable for applying a defibrillation pulse to a patient, a logic path 546 is followed to a restart block 548 at which the system is reinitialized and returned by way of a logic path 550 to the monitoring block 524.

The charging, ready and discharge blocks 536, 540 and 544 are respectively described in greater detail below in connection with FIGS. 11, 12 and 13 to provide a clearer understanding of the invention.

The control processor program passes through states which are like those of the main processor except that the control processor is not typically involved in the analyzing of the ECG signals. At initialize block 560, the control processor 142 performs self tests like those of the main processor. In addition, the input/output lines of the control processor are monitored for their correct states. This checking of the input/output lines also occurs during the operation of the defibrillator at 5 millisecond intervals. At any time a fault or failure is detected, an appropriate message is delivered to the display and, if the errors are critical, the application of defibrillation pulses to a patient is blocked. From the initialize block 560, the control processor program follows a flow path 562 to the monitoring block 564 during which time monitoring of the ECG signals is occurring by the main processor 140. If the off/disarm switch 462 is depressed, a flow path 566 is followed to the off state 568.

In addition to other messages sent between the two processors as explained below in connection with the description of the charging, ready and discharge states, a message block is sent from the main processor to the control processor every 50 milliseconds. In addition to identification information, signals representing the current main processor state, the impedance levels, the current impedance range (for example 25 to 200 ohms during the defibrillation signal application state and between 301 and 2,500 ohms during the monitoring state), the impedance, a signal indicating whether the test load is in the impedance circuit during the impedance measurement, the energy selected (via switch 310, FIG. 7), the condition of shock switch (162, FIG. 7) and the calculated discharge time for delivery of the appropriate energy for the measured impedance. In addition, the control processor is simultaneously sending identification information and other information to the main processor every 50 milliseconds, including the current state of the control processor at the time of the message, the value of VCOMP (the setting of digital analog converter 212 from 0 to 256, FIG. 1), the condition of the shock key 162 as determined by the control processor, and whether the tested impedance matches the expected value.

From the monitoring state, at block 564 (FIG. 10), if the state of the main processor 140 is set to the analyzing/charging or charging states and the impedance is in the defibrillation range, a path 570 is followed to the charging block 572. At the charging block 572, the VCOMP signal is set at a level corresponding to the appropriate level for the selected energy. When the main processor 140 reaches the ready state, and assuming the impedance is still in the defibrillation range, the control processor 142 program follows a path 574 to a ready block 576. If the main processor state reaches the discharge state, and the impedance is still in the range for defibrillation, the control and main processors both detect the depression of the shock switch 162 (FIG. 7), the control processor confirms that the computed shock discharge time is within appropriate limits to deliver the desired energy to the patient, all timer interrupts are disabled and a flow path 578 is followed by the control processor program to a discharge state 580, at which time a defibrillation pulse is applied to a patient. From blocks 572, 576, and 580, assuming the conditions for application of the defibrillation pulse to a patient have not been met, a flow path 582 is followed to a restart block 584, at which time the control processor is reinitialized and a path 586 is followed to the monitoring block 564.

Figure 11:
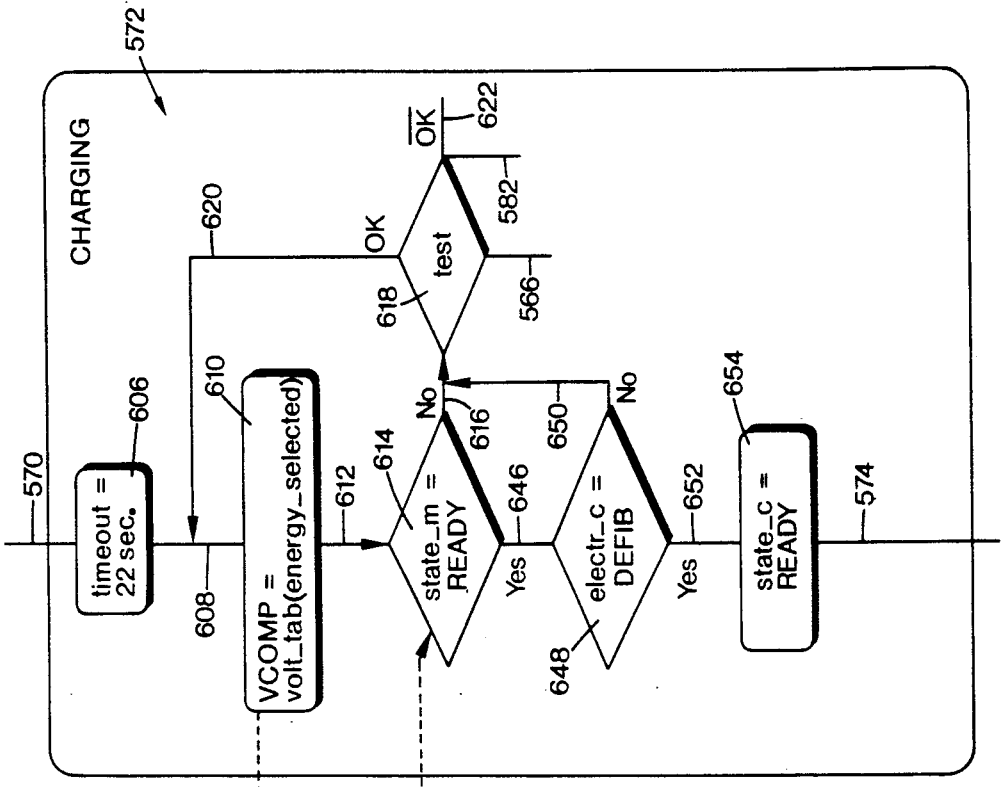
FIG. 11 is a flow chart of a charging state of the main and control processors.
Figure 11:
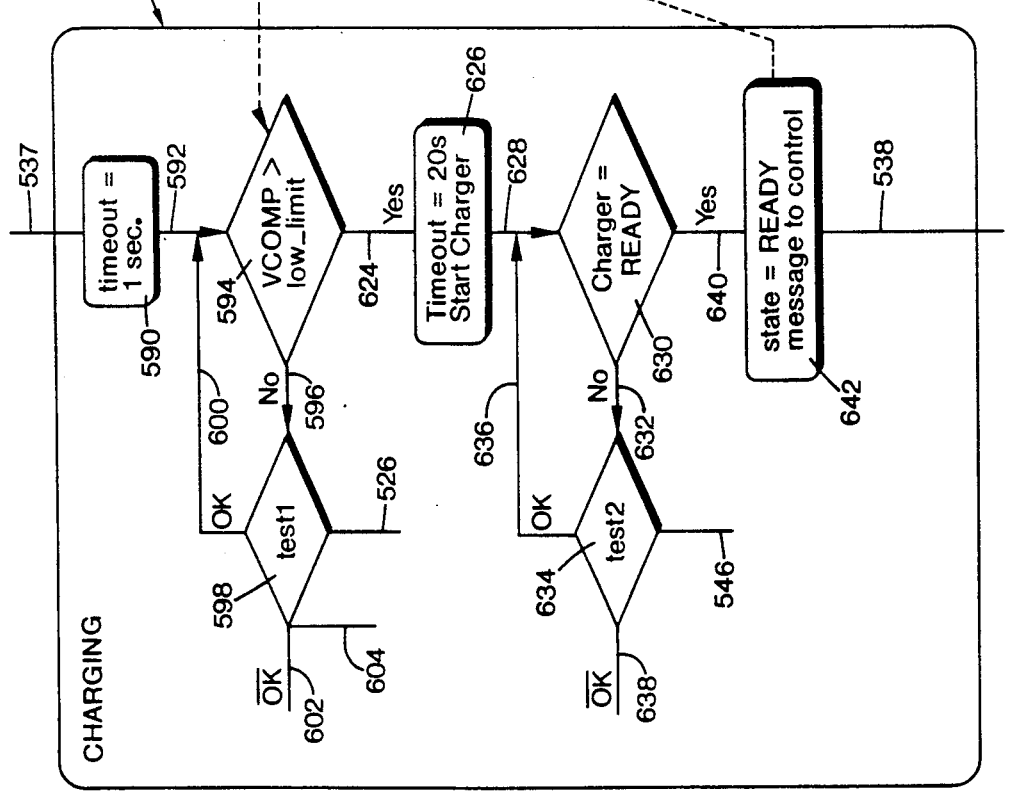

The main processor charging state block 536 and control processor charging state block 572 are best understood with reference to FIG. 11.

When the main processor reaches the charging state 536 by way of path 537, a one second timeout is established at block 590 during which time a proper VCOMP setting must be received from the control processor or an error is indicated. From block 590, a path 592 is followed to a decision block 594. At block 594, a check is made as to whether the VCOMP signal is greater than a lower limit and proper for the selected energy. Until this signal is received, a path 596 is followed to a decision block 598. At decision block 598, tests are performed and, if the test results are satisfactory, a path 600 is followed back to path 592 and the cycle continues. At decision block 598, a check is made to determine whether the impedance is proper for defibrillation. If the impedance is outside of the range for the application of a defibrillation pulse, path 602 is followed to path 546 (FIG. 10) and the system restarts. In addition, if the off switch 462 is depressed, the line 526 is followed to the block 528 (FIG. 10) and the defibrillator shuts off. If the timeout set at block 590 is reached without receiving a proper VCOMP signal from the control processor 142, or if a critical fault is detected, a line 604 is followed, the application of defibrillation pulses is blocked, and an appropriate message is displayed. Critical faults include the failure to receive the periodic messages from the control processor and improper input/output signals on lines 144 and 200 to the main processor.

At control processor charging state 572, reached from path 570, a timeout block 606 is reached and results in the setting of a timeout of 22 seconds. This timeout sets a maximum time for passage of the main processor through the charging state. If the main processor 140 does not pass through the charging state 536 within this time, an error is indicated. From timeout block 606, a path 608 is followed to the block 610. At block 610, the VCOMP level is established for the desired energy. The VCOMP setting is communicated by way of a hardware communication line 612 (from digital to analog convertor 212 and analog to digital convertor 220 in FIG. 1) to the main processor 140. From block 610, a path 612 is followed to a decision block 614 at which a check is performed to determine whether the main processor 140 has reached the next state following the charging state, namely the ready state. If the answer is no, a path 616 is followed to a decision block 618 at which an number of tests are performed. If the test results are proper, a line 620 is followed back to the path 608 and the cycle continues. At block 618, the state of the main processor 140 is verified and, if equal to the monitoring state, the path 582 (see also FIG. 10) is followed the control processor is reinitialized, and the control processor to the monitoring state. If a critical fault exists or the timeout set at block 606 occurs without the main processor progressing to the ready state, a path 622 is followed, the defibrillation pulses are blocked and a service mandatory or other appropriate message is displayed. Also, if the off switch 462 is depressed during this time, the path 566 is followed (see FIG. 10) and the defibrillator is shut off. Critical faults include the improper input/output levels to the control processor on lines 146, 202 as well as the failure to receive the periodic messages from the main processor.

From block 594 of the main processor charging state 536 (FIG. 11), after receiving the proper VCOMP signal from the control processor by way of digital to analog convertor 212 and analog to digital converter 220, (FIG. 1) a path 624 is followed to a timeout block 626. At block 626, the maximum time is set for the capacitors 10 (FIG. 2) to charge up to the desired voltage level. It normally takes the capacitors a maximum of about 10 or 11 seconds to reach the fully charged state. If they have not done so within the timeout period set at block 626, a fault is indicated. From block 626, a path 628 is followed to a decision block 630. Until the capacitors are fully charged, a path 632 is followed from blocks 630 to a test block 634 and, as long as the test results at block 634 are O.K., a path 636 is followed back to the path 628 and processing continues. At test block 634, testing of the impedance to determine that it is within the defibrillation range continues. If the impedance is incorrect, the line 546 (see also FIG. 10) is reached and the process restarts. If a critical fault is detected, a path 638 is followed with the results as indicated above. Critical faults include the incorrect input/output levels on the main processor, the failure to receive the periodic messages from the control processor and the occurrence of the timeout set at block 626.

Once the charger is ready (the capacitors are fully charged), at block 630 a path 640 is followed to a block 642. At block 642, the main processor is changed to the ready state and this fact is communicated (by way of the serial port 192, FIG. 1), as indicated by path 644 (FIG. 11) to the control processor 142 at block 614. At this time, the yes path 646 is followed from block 614 to a decision block 648 at which time the impedance is again checked to determine whether it is within the range for defibrillation. If the answer is no, a path 650 is followed back to path 616 and the process continues. If the answer is yes, a path 652 is followed to a block 654 and the control processor is shifted to the ready state.

Figure 12:
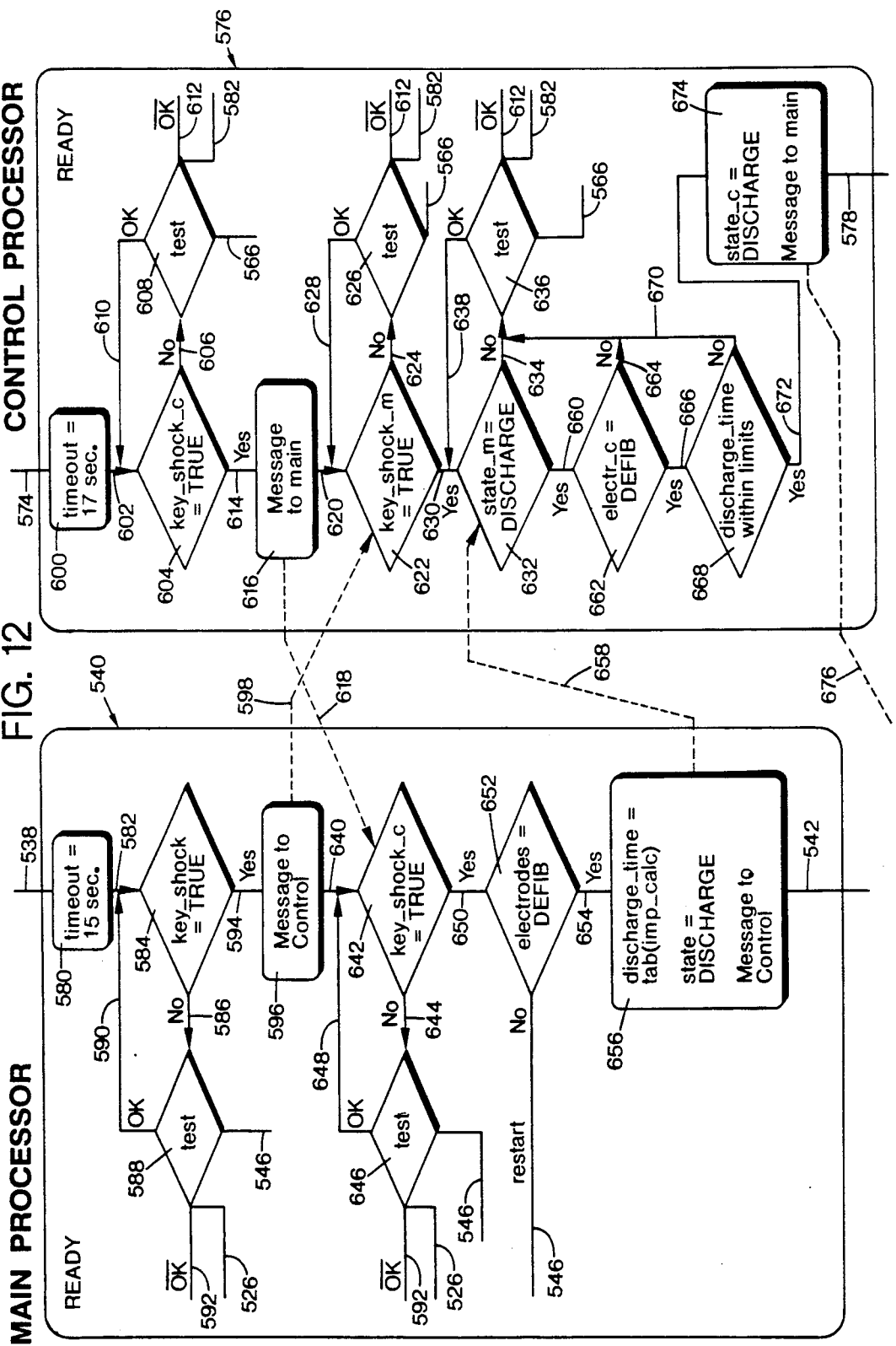
FIG. 12 is a flow chart of a ready state of the main and control processors.

At the ready state 540, a shown in FIG. 12, the main processor follows a path 538 to a timeout block 580. At block 580, a timeout is set, in this case 15 seconds, for the main processor to pass through the ready state to the discharge state 544. From block 580, a path 582 is followed to a decision block 584 at which it is determined whether the discharge switch 162 (FIG. 7) has been activated. If no, a path 586 is followed to a test block 588. If the test results are O.K., a path 590 is followed to the path 592 and processing continues. At test block 588, if the timeout set by block 580 has been reached or the impedance is outside the defibrillation range, the path 546 is followed and the system restarts (see FIG. 10). If a critical fault is determined as explained above, the path 592 is followed, the application of defibrillation pulses are blocked, and a service mandatory message or other appropriate message is displayed. If the off switch 462 is depressed during the tests at block 588, the line 526 is followed (see FIG. 10) and the defibrillator is shut off. If the shock switch 162 is depressed, indicating the operator has depressed the switch for the required minimum time, path 594 is followed to a block 596 and a message is sent by way of serial port 192 from the main processor 140 to the control processor 142 confirming the detection of the activation of the shock switch 162 by the main processor.

Figure 10:
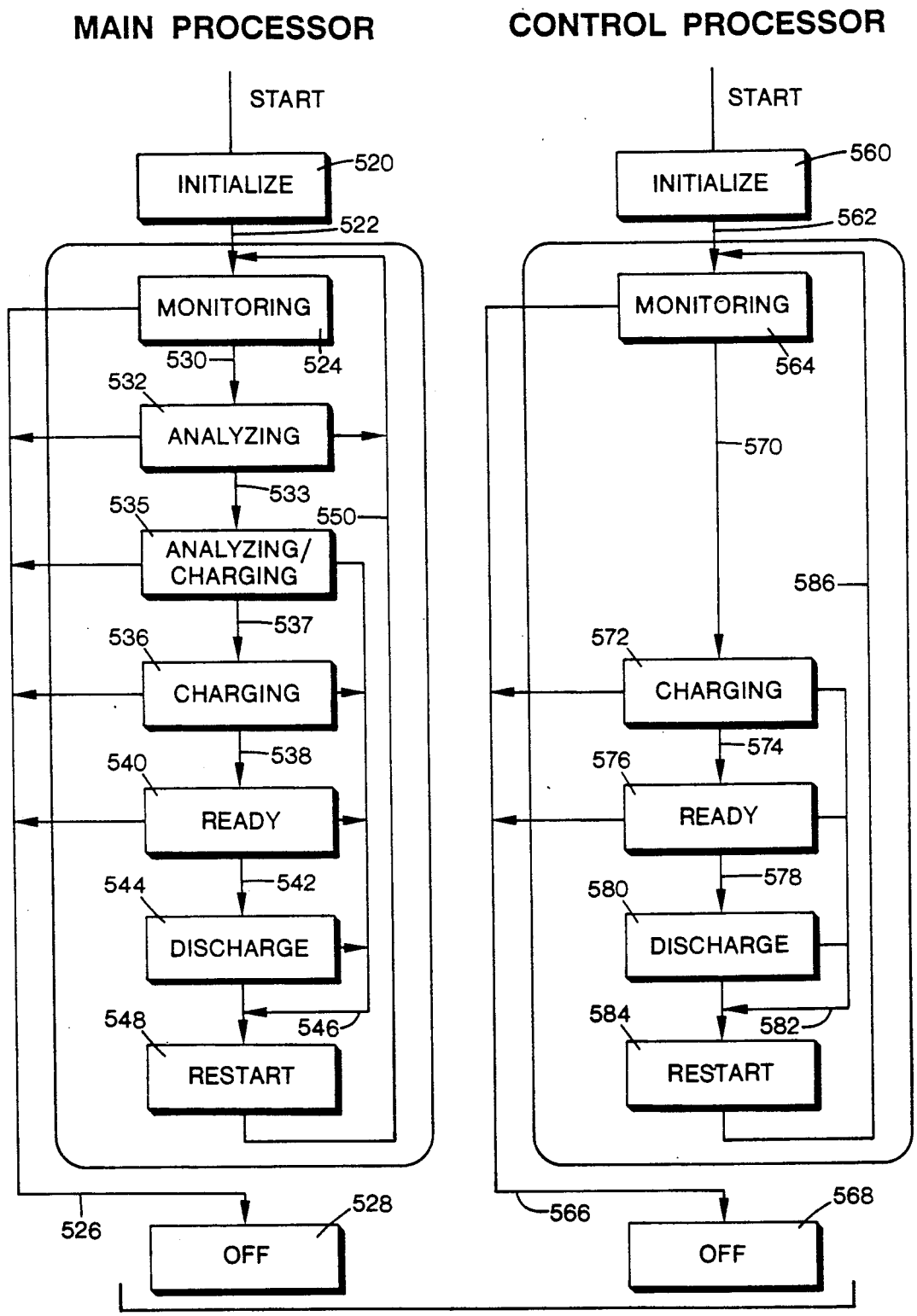
FIG. 10 is a flow chart illustrating the overall state diagram of the main and control processors of the defibrillator of FIGS. 1 and 2.

At the control processor 142, the path 574 from the charging state is followed to a timeout block 600, at which a timeout of 17 seconds is set. This time is established as the maximum time for the control processor 142 to pass from the ready state 576 to the discharge state 580. From block 600, a path 602 is followed to a decision block 604 at which point the control processor checks to see whether it has detected the activation of shock switch 162. If the answer is no, a path 606 is followed to a test block 608. If the test results at block 608 are correct, a path 610 is followed to the path 602 and processing continues. At block 608, if the timeout set at block 600 is reached or the main processor state is at the monitoring state instead of the ready state, line 582 is followed and the control processor 142 is reinitialized with the process returning to the monitoring block as shown in FIG. 10. If the off switch 462 is depressed during this time, line 566 is followed and the system is shut off (see FIG. 10). If a critical fault is detected, as explained above, line 612 is followed from block 608 with the application of defibrillation pulses being blocked and an appropriate service mandatory or other message being displayed.

From block 604, if the control processor 142 has received a signal indicating the activation of the shock switch 162, a path 614 is followed to a block 616 and a message is sent to the main processor as indicated by line 618. This message indicates that the control processor has determined that the switch 162 has been activated. From block 616, the control processor follows a path 620 to a block 622 where it receives confirmation via line 598 that the main processor has also detected the activation of the switch 162. If this message has not been detected, path 624 is followed to a test block 626 which repeats the tests performed at block 608. If the test results are O.K., a path 628 is followed back to the path 620. Otherwise, the paths 566, 582 or 612 are followed, as explained above. Assuming at block 622 that the shock switch activation message on line 598 has been received from the main processor, then a path 630 is followed to a decision block 632. At block 632, a determination is made as to whether the main processor has shifted from the ready state to the discharge state. If not, a path 634 is followed to a test block 636 at which the tests of block 608 are repeated. If the tests at the block 636 produce proper results, a path 638 is followed to the path 630 and processing continues. If the results are otherwise at block 636, the respective lines 566, 582 and 612 are followed.

At the main processor ready state, from block 596, a path 640 is followed to a decision block 642 which asks whether the control processor message indicating the activation of shock switch 162 has been delivered by way of serial port 192 (FIG. 1) to the main processor. If the answer is no, a path 644 is followed to a test block 646, which performs the test indicated above in connection with block 588. If the test results are proper, a path 648 is followed back to the path 640 and processing continues. If the results are otherwise, the lines 546, 526 and 592 are followed as explained above in connection with block 588.

Upon detection of the message on line 618 at block 642, the main processor program follows a path 650 to a decision block 652. At block 652, another check is made as to whether the impedance at the electrodes is within the proper range for the application of a defibrillation pulse. If not, line 546 is followed (see FIG. 10) and processing is restarted. If the answer is yes, a path 654 is followed to a block 656. At block 656, the discharge time is calculated by the main processor for delivery of the selected energy to the patient during a defibrillation pulse. In addition, the state of the main processor is shifted from the ready state to the discharge state. Finally, a message is sent as indicated by line 658 (and via the serial port 192, FIG. 10), to block 632 of the control processor ready state program. In addition, the main processor proceeds to the discharge state 544 as indicated in FIG. 13. Upon the shifting of the main processor to the discharge state, the control processor follows the yes path 660 from block 632 to a decision block 662. At block 662, another check is made to determine whether the impedance at the electrodes is within the defibrillation range. If not, a path 664 is followed back to the block 634 and processing continues. If the answer is yes, a path 666 is followed to a decision block 668. At block 668, a determination is made as to whether the discharge time calculated by the main processor at block 656 is within the discharge time limits. If not, a line 670 is followed back to the line 634 and processing continues. This provides still another check on the proper functioning of the main processor 140 as discharge pulse time limits outside of acceptable time limits indicate that a processing error has occurred. If the discharge time is within the limits at block 668, a path 672 is followed to a block 674. At block 674, the control processor is shifted from the ready state to the discharge state. In addition, a message is sent to the main processor 140 via serial port 192 (FIG. 10) and as indicated by line 676 in FIG. 12, that the control processor 142 is at the discharge state.

Figure 13:
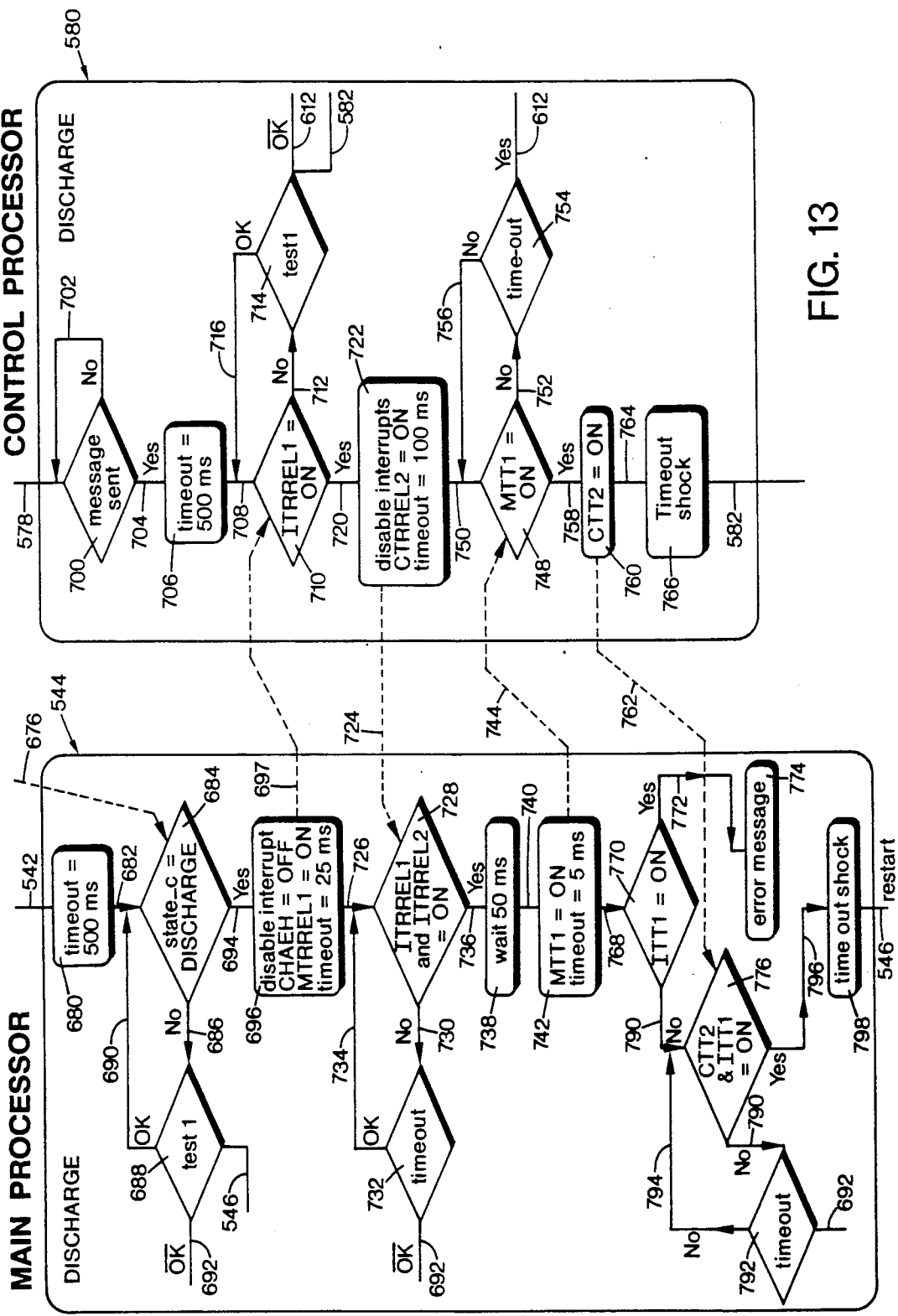
FIG. 13 is a flow chart of a discharge state of the main and control processors.

With reference to FIG. 13, when in the discharge state 544, the main processor follows path 542 to a timeout block 680. At block 680, a maximum time is set at 500 milliseconds, in this example. During this time a shock must be delivered to a patient or the main processor 140 will shift states. From block 680, a path 682 is followed to a decision block 684 which checks to see whether the control processor has reached the discharge state, as determined from the signal on line 676. If the answer is no, a path 686 is followed to a test block 688 during which time tests are made. If the tests results are proper, a path 690 is followed back to path 682 and processing continues. At test block 688, the electrodes are again checked to determine whether they are in the defibrillation range. If not, the line 546 is followed and processing is restated (see FIG. 10). If the timeout set by block 680 is reached, a line 692 is followed at which time a service mandatory or other appropriate message is indicated and the application of defibrillation pulses are blocked.

Upon a determination at block 684 that the control processor has entered the discharge state 580, a path 694 is followed from block 684 to a block 696. At block 696, interrupts are disabled. That is, communication along the serial port 192 from the control processor to the main processor is interrupted, testing of the input/output lines to the main processor is interrupted and impedance testing is stopped. In addition, the channel enable signal is checked to determine that it is off, indicating that the charging of the capacitors is not occurring. In addition, the transfer relay control signal from the main processor 140 (MTRREL1 in FIG. 13) is checked to determine that it is on. Also, a timeout of 25 milliseconds is set to provide time for the control processor 142 to activate the transfer relay 30 by way of the signal on line TRREL2 (FIG. 1). In addition, as indicated by line 697, the control processor detects the occurrence of the MTRREL1 signal (via line 146b in FIG. 3).

At discharge block 580, the control processor 142 via path 578, reaches a decision block 600 which checks to determine whether the maessage has been sent to the main processor that the control processor is in the discharge state. If the answer is no, a path 702 is followed back to block 700. If the answer is yes, a path 704 is followed to a block 706 at which a timeout of 500 milliseconds is set. This is the maximum time allowed for the activation of the first transfer relay 16 by the main processor 140. From block 706, by way of a path 708, a decision block 710 is reached at which time a determination is made as to whether the first transfer relay 16 is enabled, that is whether the TRREL1 signal has been provided. If the answer is no, a path 712 is followed to a decision block 714 at which tests are performed. If the test results are proper, a path 716 is folowed back to the path 708. If at block 714 the main processor state is determined to be in the monitoring state, for example because of a return of the main processor to the monitoring state during processing, the path 582 is followed and the control processor returns to the monitoring state (see FIG. 10). If the timeout set by block 706 is reached, a path 612 is followed from blocks 714 with the result as described above. Upon the detection of the TRREL1 signal by the control processor at block 710, a path 720 is followed to a block 722. At block 722, interrupts are disabled. Specifically, the serial port commuincation 192 (FIG. 1) from the main processor to the control processor is closed, testing of the input/outputs of the control processor is stopped. In addition, the control processor produces a transfer relay control signal output (CTRREL2) for purposes of enabling the second transfer relay 30 (FIG. 2). The control processor verifies the occurrence of this signal, e.g. by way of line 146c in FIG. 3. In addition, a timeout is set at 100 milliseconds, a maximum amount of time for the switching transistor 36 (FIG. 2) to be activated. In addition, the main processor, as indicated by hardware communication line 724 in FIG. 13, detects the presence of the TRREL2 signal from the control processor (see also line 144b in FIG. 3).

From block 696, the main processor program follows a path 726 to a decision block 728. At block 728, the question is asked as to whether each of the transfer relay signals has occurred. If the answer is no, a path 730 is followed to a decision block 732. At block 732, a check is made as to whether the timeout set as block 696 has occurred. If not, path 734 is followed and processing continues. If so, the path 692 is followed as explained above. Assuming both of the transfer relay signals (TRREL1 and TRREL2) have occurred, then a path 736 is followed to a block 738 and a wait period is established. Specifically, a 50 millisecond wait period is established at block 738 for trhe transfer relays 16 and 30 to stabilize. From block 738, a block 742 is reached, by way of path 740, at which time the transfer switch control signal is provided on line 200a (FIG. 4). In addition, a timeout is set at 5 milliseconds to allow the control processor to produce a corresponding transfer switch control signal. The occurrence of the transfer switch signal from the main processor is communicated, as indicated by hardware link 744, to a decision block 748 of the control processor. Decision block 748 is coupled by a line 750 to the block 722. At block 748, a determination is made as to whether the transfer switch signal has been received from the main processor. If not, a path 752 is followed to a decision block 754. At block 754, a query is made as to whether the timeout set at block 722 has been reached. If not, a path 756 is followed back to the path 750 and processing continues. If the answer is yes, the path 612 is followed as explained above.

Upon the occurrence of the transfer switch signal from the main processor 140, a path 758 is followed from the block 748 to a block 760. At block 760, the transfer switch signal from the control processor is provided on line 202a (see FIG. 4). The existence of this signal is communicated by way of a hardware link, indicated at 762 in FIG. 13 (see also line 200b in FIG. 4) to a block 776 in the main processor discharge program. From block 760, a path 764 is followed to a timeout shock 766 which waits for a sufficient time for the delivery of the defibrillation pulse to the patient before the line 582 is reached and the control processor returns to the restart block 584 (FIG. 10) with processing continuing.

From block 742, the main processor follows a path 768 to a decision block 770. At block 770, a determination is made as to whether the AND gate 432 (FIG. 4) is on with only the signal from line 200a of the main processor 140 (FIG. 4). That is, if the TTI signal on line 44 is present as a result of only the transfer switch control signal from the main processor, an error is indicated. This occurs by way of path 772 from block 770 to an error message block 774. If the answer at the query at block 770 is no, indicating that the TTI signal on line 44 is not occurred as a result of the receipt of only the transfer switch signal from the main processor, a path 790 is followed to the decision block 776. At block 776, the question is asked as to whether the switch transfer signals have been detected from both the main processor 140 and the control processor 142. If the answer is no, a path 790 is followed to a decision block 792. At block 792, a check is made as to whether the timeout set at block 742 has been met. If the answer is no, a path 794 is followed to path 790 and processing continues. If the answer is yes, from block 792 the path 692 is followed as a failure of the defibrillator has been detected. If at block 776, the transfer switch control signals have been received from each of the main and control processors 140, 142, a path 796 is followed to a block 798 and a shock of the appropriate length is delivered to the patient. From block 798, the restart line 546 (see FIG. 10) is reached and processing continues.

Although the defibrillator has been described in connection with suitable programming for the main and control processors 140, 142, it should be apparent to those of ordinary skill in the art that this program may be varied in many respects without departing from the principles of the present invention. More specifically, the present invention is intended to provide a defibrillator with reliability and verification checking which enables the detection of potential faults or failures that, if unchecked, could result in the inappropriate delivery of defibrillation pulses to a patient.

Having illustrated and described the principles of our invention with reference to several preferred embodiments, it should be apparent to those of ordinary skill in the art that our invention may be modified in arrangement and detail without departing from its principles. We claim all such modifications within the scope of the following claims.

I claim:

1. A defibrillator for applying a defibrillation pulse to a patient suffering from cardiac distress comprising:

a high voltage source;

a defibrillator pulse discharge circuit for coupling the high voltage source in a series circuit with the patient to selectively deliver a defibrillation pulse from the high voltage source to the patient, the discharge circuit including at least one relay means responsive to a transfer relay signal for shifting from a first position in which the relay means opens the series circuit to a second position in which the relay means closes to permit the passage of the defibrillation pulse to the patient;

treatment indicating means for providing a treatment indicating signal corresponding to the patient being in a condition of cardiac distress of the type appropriate for the application of a defibrillation pulse to the patient;

control circuit means coupled to the treatment indicating means and to the relay means for providing the transfer relayu signal in response to the treatment indicating signal, the control circuit means including a first processor responsive to the treatment indicating signal and having a first output for providing a first relay control signal in response to the treatment indicating signal, a second processor responsive to the treatment indicating signal and having a first output for producing a second relay control signal in response to the treatment indicating signal, the control circuit means also including a transfer relay circuit coupled to the respective first outputs of the first and second processors for receiving the first and second relay control signals, the transfer relay circuit having at least one transfer relay signal output at which the transfer relay signal is provided in response to the receipt of both of the first and second relay control signals, whereby the relay means is in the open position so as to block the application of a defibrillator pulse to the patient in the event of an improper relay control signal from only one processor.

2. A defibrillator apparatus according to claim 1 in which the relay means comprises a relay with first and second relay switches each shifting from first to second positions in response to a common transfer relay signal.

3. A defibrillator apparatus according to claim 1 in which the relay means comprises a first transfer relay in the series circuit and responsive to a first transfer relay signal for shifting from the first position to the second position, the relay means also comprising a second transfer relay in the series circuit and responsive to a second transfer relay signal for shifting from the first position to the second position, the transfer relay circuit providing an output of first and second transfer relay signals, the first transfer relay signal being provided by the transfer relay circuit in response to the first relay control signal and the second transfer relay signal being provided by the transfer relay circuit in response to the second relay control signal.

4. A defibrillator apparatus according to claim 3 in which the second processor has a second input for receiving the first transfer relay signal, the second processor comprising means for preventing the delivery of the second transfer relay signal until the detection of the first transfer relay signal.

5. A defibrillator apparatus according to claim 4 in which the first processor has a second input for receiving the second transfer relay signal, the first processor comprises means for terminating the first transfer relay signal in the absence of the occurrence of the second transfer relay signal within a predetermined time of the occurrence of the first transfer relay signal.

6. A defibrillator apparatus according to claim 5 in which the first processor includes a third input coupled to the transfer relay circuit for receiving the first transfer relay signal, the first processor means comprising means for confirming the occurrence of the first transfer relay signal in response to the first relay control signal, the second processor having a third input coupled to the transfer relay circuit for receiving the second transfer relay signal, the second processor comprising means for confirming the occurrence of the second transfer relay signal in response to the second relay control signal.

7. A defibrillator apparatus according to claim 3 in which the first processor includes an input coupled to the relay transfer circuit for receiving the first transfer relay signal, the first processor means comprising means for confirming the occurrence of the first relay transfer signal in response to the first relay control signal, the second processor having an input coupled to the relay control circuit for receiving the second transfer relay signal, the second processor comprising means for confirming the occurrence of the second transfer relay signal in response to the second relay control signal.

8. A defibrillator apparatus according to claim 1 in which the treatment indicating means comprises a manually activated treatment initiator which produces the treatment indicating signal upon activation thereof.

9. A defibrillator according to claim 8 in which the manually activated treatment initiator comprises a shock initiating switch.

10. A defibrillator apparatus according to claim 8 in which the treatment indicating means comprises ECG monitoring means coupled to the patient for receiving ECG signals from the patient, the treatment indicating means also comprising means responsive to the ECG signals for determining and indicating the occurrence of cardiac distress in the patient of the type which is appropriate for treatment with a defibrillation pulse, the manually activated treatment initiator being activated in response to the indication of such cardiac distress.

11. A defibrillator apparatus according to claim 1 in which the treatment indicating means includes an ECG monitoring means coupled to the patient for receiving ECG signals from the patient, the treatment indicating means also comprising means responsive to the ECG signals for producing the treatment indicating signals in response to ECG signals corresponding to cardiac distress in the patient of the type which is appropriate for treatment by a defibrillation pulse, the control circuit means comprising means automatically responsive to the treatment indicating signals for producing the first and second relay control signals.

12. A defibrillator apparatus according to claim 1 in which the defibrillator pulse discharge circuit includes an electronic switch in the series circuit, the electronic switch being responsive to a transfer switch signal for switching from a first state in which the series circuit is electrically nonconducting through the electronic switch to a second state in which the series circuit is electrically conducting through the electronic switch, the first processor including a first switch control signal output and comprising means for providing a first switch control signal at such output in response to the treatment indicating signal, the second processor including a second switch control signal output and comprising means for providing a second switch control signal at such output in response to the treatment indicating signal, transfer switch circuit means coupled to the first and second processors and responsive to the first and second switch control signals for providing the switch transfer signal in response to the occurrence of both of the first and the second switch control signals, whereby an improper switch control signal from only one of the processors is insufficient to cause the transfer switch circuit means to provide the transfer switch signal.

13. A defibrillator apparatus according to claim 12 in which the first processor has an input for receiving the second switch control signal, the first processor comprising means for confirming the occurrence of the second switch control signal, the second processor having an input for receiving the first switch control signal, the second processor comprising means for confirming the occurrence of the first switch control signal, the second processor also comprising means for preventing the occurrence of the second switch control signal until the occurrence of the first switch control signal, and the first processor comprising means for terminating the first switch control signal in the absence of the occurrence of the second switch control signal within a predetermined time following the occurrence of the first switch control signal.

14. A defibrillator apparatus according to claim 13 in which each of the first and second processors has a respective input coupled to the transfer switch circuit means for receiving the transfer switch signal, the first and second processors comprising means for confirming the occurrence of the transfer switch signal in response to the first and second switch control signals.

15. A defibrillator apparatus according to claim 12 including voltage monitoring circuit means for monitoring the voltage at the electronic switch, and at least one of the processors being coupled to the voltage monitoring circuit means and comprising means for preventing the application of the defibrillation pulse in the event the voltage at the electronic switch means is at an undesired magnitude.

16. A defibrillator apparatus according to claim 12 in which the electronic switch comprises two electronic switch elements, each switch element being positioned in the series circuit with a circuit node point in the series circuit therebetween, the switch elements each being shiftable in response to the transfer switch signal from a first condition in which the series circuit is electrically nonconducting through the switch element to a second condition in which the series circuit is electrically conducting through the switch element, at least one of the first and second processors having a voltage monitoring input, the defibrillator apparatus including voltage measuring circuit means for monitoring the voltage at the circuit node and for producing a voltage monitoring output signal to the voltage monitoring input, the processor receiving the voltage monitoring output signal comprising means for the blocking switch control signal from such processor in the event the voltage monitored at the circuit node differs from a desired voltage magnitude, whereby monitoring of the voltage at the circuit node permits the detection of a failure of the electronic switch elements.

17. A defibrillator apparatus according to claim 16 in which the high voltage source includes capacitor charge storage means and charging circuit means for charging the capacitor charge storage means, the voltage measuring circuit means includes means for receiving as inputs a signal corresponding to the voltage at the capacitor charge storage means and a signal corresponding to the voltage monitored at the electronic switch, the voltage measurement circuit means comprising means for comparing such inputs and for producing a voltage monitoring output signal corresponding to the compared voltages.

18. A defibrillator circuit according to claim 1 including impedance measurement circuit means coupled to the first processor for measuring the impedance in the series circuit across the patient, the impedance measurement circuit means including means responsive to an impedance control signal for placing a known impedance load in the impedance measurement circuit, the first processor comprising means for providing the impedance control signal, the first processor also comprising means for comparing the impedance determined without the known load to the impedance determined with the known load to verify the consistency of the impedance measurements and thereby the accuracy of the impedance measurement circuit.

19. A defibrillator apparatus according to claim 18 in which the first processor comprises means for blocking the application of the defibrillation pulse in the event the impedances determined with and without the known load are inconsistent.

20. A defibrillator for applying a defibrillation pulse to a patient suffering from cardiac distress comprising:
a high voltage source;
a defibrillator pulse discharge circuit for coupling the high voltage source in a series circuit with the patient to selectively deliver a defibrillation pulse from the high voltage source to the patient, the discharge circuit including at least one relay means responsive to a transfer relay signal for shifting from a first position in which the relay means opens the series circuit to a second position in which the relay means closes to permit the passage of the defibrillation pulse to the patient;
treatment indicating means for providing a treatment indicating signal corresponding to the patient being in a condition of cardiac distress of the type appropriate for the application of a defibrillation pulse to the patient;
control circuit means coupled to the treatment indicating means and to the relay means for providing the transfer relay signal in response to the treatment indicating signal, the control circuit means including a first processor responsive to the treatment incicating signal and having a first output for providing a first relay control signal in response to the treatment indicating signal, a second processor responsive to the treatment indicating signal and having a first output for producing a second relay control signal in response to the treatment indicating signal, the control circuit means also including a transfer relay circuit coupled to the respective first outputs of the first and second processors for receiving the first and second relay control signals, the transfer relay circuit having a first transfer relay signal output at which a first transfer relay signal is provided and a second transfer relay signal output at which a second transfer relay signal is provided, the first and second transfer relay signal being provided in response to the receipt of both of the first and second relay control signals, whereby the relay means is in the open position so as to block the application of a defibrillator pulse to the patient in the event of an improper relay control signal from only one processor;
the first processor including an input coupled to the transfer relay circuit for receiving the first transfer relay signal, the first processor means comprising means for confirming the occurrence of the first transfer relay signal in response to the first relay control signal, the second processor having an input coupled to the transfer relay circuit for receiving the second transfer relay signal, the second processor comprising means for confirming the occurrence of the second transfer relay signal in response to the second relay control signal;
the defibrillator pulse discharge circuit including an electronic switch in the series circuit, the electronic switch being responsive to a transfer switch signal for switching from a first state in which the series circuit is electrically nonconducting through the electronic switch to a second state in which the series circuit is electrically conducting through the electronic switch, the first processor including a first switch control signal output and comprising means for providing a first switch control signal at such output in response to the treatment indicating signal, the second processor including a second switch control signal output and comprising means for providing a second switch control signal at such output in response to the treatment indicating signal, transfer switch circuit means coupled to the first and second processors and responsive to the first and second switch control signals for providing the transfer switch signal in response to the occurrence of both of the first and the second switch control signals, whereby an improper switch control signal from only one of the processors is insufficient to cause the transfer switch circuit means to provide the transfer switch signal;
the electronic switch comprising two electronic switch elements, each switch element being positioned in the series circuit with a circuit node point in the series circuit therebetween, the switch elements each being shiftable in response to the transfer switch signal from a first condition in which the series circuit is electrically nonconducting through the switch element to a second condition in which the series circuit is electrically conducting through the switch element, at least one of the first and second processors having a voltage monitoring input, the defibrillator apparatus including voltage measuring circuit means for monitoring the voltage at the circuit node and for producing a voltage monitoring output signal to the voltage monitoring input, the said at least one of the first and second processors receiving the voltage monitoring output signal comprising means for blocking the switch control signal from such processor in the event the voltage monitored at the circuit node differs from a desired voltage level, whereby monitoring of the voltage at the circuit node permits the detection of a failure of the electronic switch elements.

21. A defibrillator apparatus according to claim 20 in which the high voltage source includes capacitor charge storage means and charging circuit means for charging the capacitor charge storage means, the voltage measuring circuit means includes means for receiving as inputs a signal corresponding to the voltage at the capacitor charge storage means and a signal corresponding to the voltage at the circuit node, the voltage measurement circuit means comprising means for comparing the voltage at the circuit node with the voltage at the capacitor charge storage means and for producing an output in the event that the relative voltages at the capacitor charge storage means and circuit node are outside of a predetermined range, the voltage measuring circuit means producing a voltage monitoring output signal corresponding to the compared voltages.

22. In a defibrillator for applying a defibrillation pulse in a series circuit including a patient suffering from cardiac distress, an impedance measurement circuit means for measuring the impendance in the series circuit across the patient, the impedance measurement circuit means including means responsive to an impedance control signal for placing a known impedance load in the impedance measurement circuit, a processor comprising means for providing the impedance control signal, the processor also comprising means for comparing the impedance determined without the known load to the impedance determined with the known load and for verifying the consistency of the impedance measurements and thereby the accuracy of the impedance measurement circuit.

23. A defibrillator apparatus for applying a defibrillation pulse to a patient suffering from cardiac distress comprising:
    a high voltage source;
    a defibrillator pulse discharge circuit for coupling the high voltage source in a series circuit with the patient to selectively deliver a defibrillation pulse from the high voltage source to the patient, the discharge circuit including at least one relay means responsive to a transfer relay signal for shifting from a first position in which the relay means opens the series circuit to a second position in which the relay means closes to permit the passage of the defibrillation pulse to the patient;
    treatment indicating means for providing a treatment indicating signal corresponding to the patient being in a condition of cardiac distress of the type appropriate for the application of a defibrillation pulse to the patient;
    control circuit means coupled to the treatment indicating means and to the relay means for providing the transfer relay signal in response to the treatment indicating signal, the control circuit means including a first processor responsive to the treatment indicating signal and having a first output for providing a first relay control signal in response to the treatment indicating signal, a second processor responsive to the treatment indicating signal and having a first output for producing a second relay control signal in response to the treatment indicating signal, the control circuit means also including a transfer relay circuit coupled to the respective first outputs of the first and second processors for receiving the first and second relay control signals, the transfer relay circuit having at least one transfer relay signal output at which the transfer relay signal is provided in response to the receipt of both of first and second relay control signals, whereby the relay means is in the open position so as to block the application of a defibrillator pulse to the patient in the event of an improper relay control signal from only one processor;
    the high voltage source including capacitor charge storage means and charging circuit means for charging the capacitor charge storage means;
    the defibrillator pulse discharge circuit including an electronic switch in the series circuit, the electronic switch being responsive to a transfer switch signal for switching from a first state in which the series circuit is electrically nonconducting through the electronic switch to a second state in which the series circuit is electrically conducting through the electronic switch, the first processor including a first switch control signal output and comprising means for providing a first switch control signal at such output in response to the treatment indicating signal, the second processor including a second switch control signal output and comprising means for providing a second switch control signal at such output in response to the treatment indicating signal, transfer switch circuit means coupled to the first and second processors and responsive to the first and second switch control signals for providing the electronic transfer switch signal in response to the occurrence of both the first and the second switch control signals, whereby an improper switch control signal from only one of the processors is insufficient to cause the transfer switch circuit means to provide the transfer switch signal;
    at least one of the first and second processors having a voltage monitoring input;
    the defibrillator apparatus including voltage measuring circuit means for measuring the voltage at the electronic switch and for producing a voltage measuring output signal to the voltage monitoring input, the processor which receives the voltage monitoring input comprising means for blocking the application of the defibrillation pulse to the patient in the event the voltage measured at the electronic switch differs from a desired voltage level, whereby monitoring of the voltage at the electronic switch permits the detection of a failure of the electronic switch.

24. A defibrillator for applying a defibrillation pulse to a patient suffering from cardiac distress comprising:
    a high voltage source;
    a defibrillator pulse discharge circuit for coupling the high voltage source in a series circuit with the patient to selectively deliver a defibrillation pulse from the high voltage source to the patient, the discharge circuit including at least one relay means responsive to a transfer relay signal for shifting from a first position in which the relay means opens the series circuit to a second position in which the relay means closes to permit the passage of the defibrillation pulse to the patient;
    treatment indicating means for providing a treatment indicating signal corresponding to the patient being in a condition of cardiac distress of the type appropriate for the application of a defibrillation pulse to the patient;

control circuit means coupled to the treatment indicating means and to the relay means for providing the transfer relay signal in response to the treatment indicating signal;

the high voltage source comprising capacitor charge storage means for storing high voltage and capacitor charging circuit means for charging the capacitor charge storage means;

ECG monitoring means for coupling to the patient to receive ECG signals from the patient;

power switch means which has an off or inactive state, the power switch means comprising means for preventing the charging of the capacitor charge storage means and the monitoring of the ECG signals from the patient by the ECG monitoring means when the power switch is in the off state;

data storage means;

a manually activated event marker switch coupled ot the data storage means for causing the entry of a marker into the data storage means in response to the manual activation of the event marker;

a real time clock for providing a clock output comprising time and date information;

means for supplying power to the event marker switch and to the clock independently of the state of the power switch means; and activation of the event marker switch causing the entry of time and date data and the marker into the data storage means when the power switch means is in the off state.

25. A defibrillator for applying a defibrillation pulse to a patient suffering from cardiac distress comprising:

a high voltage source;

a defibrillator pulse discharge circuit for coupling the high voltage source in a series circuit with the patient to selectively deliver a defibrillation pulse from the high voltage source to the patient, the discharge circuit including at least one relay means responsive to a transfer relay signal for shifting from a first position in which the relay means opens the series circuit to a second position in which the relay means closes to permit the passage of the defibrillation pulse to the patient;

treatment indicating means for providing a treatment indicating signal corresponding to the patient being in a condition of cardiac distress of the type appropriate for the application of a defibrillation pulse to the patient;

control circuit means coupled to the treatment indicating means and to the relay means for providing the transfer relay signal in response to the treatment indicating signal, the control circuit means including a first processor responsive to the treatment indicating signal and having a first output for providing a first relay control signal in response to the treatment indicating signal, a second processor responsive to the treatment indicating signal and having a first output for producing a second relay control signal in response to the treatment indicating signal, the control circuit means also including a transfer relay circuit coupled to the respective first outputs of the first and second processors for receiving the first and second relay control signals, the transfer relay circuit having at least one transfer relay signal output at which the transfer relay signal is provided in response to the receipt of both of first and second relay control signals, whereby the relay means is in the open position so as to block the application of a defibrillator pulse to the patient in the event of an improper relay control signal from only one processor;

the relay means comprising a first transfer relay in the series circuit and responsive to a first transfer relay signal for shifting from the first open position to the second closed position and a second transfer relay in the series circuit and responsive to a second transfer relay signal for shifting from the first open to the second closed position, the transfer relay circuit providing as outputs first and second transfer relay signal, the first transfer relay signal being provided by the transfer relay circuit in response to the first relay control signal and the second transfer relay signal being provided by the transfer relay circuit in response to the second relay control signal;

the defibrillator pulse discharge circuit including an electronic switch in the series circuit, the electronic switch being responsive to a transfer switch signal for switching from a first state in which the series circuit is electrically nonconducting through the electronic switch to a second state in which the series circuit is electrically conducting through the electronic switch, the first processor including a switch control signal output and comprising means for providing a first switch control signal at such output in response to the treatment indicating signal, the second processor including a switch control signal output and comprising means for providing a second switch control signal at such output in response to the treatment indicating signal, transfer switch circuit means coupled to the first and second processor and responsive to the first and second switch control signals for providing the transfer switch signal in response to the occurrence of both of the first and the second switch control signals, whereby an improper switch control signal from only one of the processors is insufficient to cause the electronic transfer switch circuit means to provide the transfer switch signal;

an impedance measurement circuit means for measuring the impedance in the series circuit across the patient, the impedance measurement circuit means including means responsive to an impedance control signal for placing a known impedance load in the impedance measurement circuit, a processor comprising means for providing the impedance control signal, the processor also comprising means for comparing the impedance determined without the known load to the impedance determined with the known load and for verifying the consistency of the impedance measurements and thereby the accuracy of the impedance measurement circuit; and the first processor comprises means for blocking the transfer switch signal in the event the impedances determined with and without the known load are inconsistent.

26. A defibrillator apparatus according to claim 25 in which the second processor has a second input coupled to the transfer relay circuit for receiving the first transfer relay signal, the second processor comprising means for preventing the delivery of the second transfer relay signal until the detection of the first transfer relay signal;

the first processor having a second input coupled to the transfer relay circuit for receiving the second transfer relay signal, the first processor comprising means for terminating the first transfer relay signal in the absence of the occurrence of the second transfer relay signal within a predetermined time of the occurrence of the first transfer relay signal.

27. A defibrillator apparatus according to claim 26 in which the first processor includes a third input coupled to the transfer relay circuit for receiving the first transfer relay signal, the first processor means comprising means for confirming the occurrence of the first transfer relay signal in response to the first relay control signal, the second processor having a third input coupled to the transfer relay circuit for receiving the second transfer relay signal, the second processor comprisign means for confirming the occurrence of the second transfer relay signal in response to the second relay control signal.

28. A defibrillator apparatus according to claim 27 in which the high voltage source comprises capacitor charge storage means for storing high voltage and capacitor charging circuit means for charging the capacitor charge storage means;

the apparatus also including ECG monitoring means for coupling to the patient to receive ECG signals from the patient;

power switch means which has an off or inactive state, the power switch means comprising means for preventing the charging of the capacitor charge storage means and the monitoring of the ECG signals from the patient by the ECG monitoring means when the power switch means is in the off state;

data storage means;

manually activated event marker means coupled to the data storage means for causing the entry of a marker into the data storage means in response to the manual activation of the event marker means;

real time clock means for providing a clock output comprising time and date information;

means for supplying power to the event marker means and to the clock means independently of the state of the power switch means;

activation of the event marker means causing the entry of time and date data and the marker into the data storage means when the power switch means is in the off position.

* * * * *